US012797245B2

(12) United States Patent
Merrill et al.

(10) Patent No.: US 12,797,245 B2
(45) Date of Patent: Nov. 17, 2026

(54) WEIGHTED, COOLING SLEEP MASK

(71) Applicants: Ashley Merrill, Santa Monica, CA (US); Jaime Carlson, Santa Monica, CA (US); Hilda Chang, Walnut Creek, CA (US)

(72) Inventors: Ashley Merrill, Santa Monica, CA (US); Jaime Carlson, Santa Monica, CA (US); Hilda Chang, Walnut Creek, CA (US)

( * ) Notice: Subject to any disclaimer, the term of this patent is extended or adjusted under 35 U.S.C. 154(b) by 566 days.

(21) Appl. No.: 17/511,533

(22) Filed: Oct. 26, 2021

(65) Prior Publication Data

US 2023/0131013 A1 Apr. 27, 2023

(51) Int. Cl.
*A61F 9/04* (2006.01)
*A61F 7/00* (2006.01)
*A61F 7/02* (2006.01)

(52) U.S. Cl.
CPC .............. *A61F 9/04* (2013.01); *A61F 7/0241* (2013.01); *A61F 2007/0003* (2013.01); *A61F 2007/0004* (2013.01); *A61F 7/02* (2013.01)

(58) Field of Classification Search
CPC ...... A61F 2007/0003; A61F 2007/0004; A61F 7/02; A61F 7/0241; A61F 2007/0263; A61F 2007/0268; A61F 9/04
See application file for complete search history.

(56) References Cited

U.S. PATENT DOCUMENTS

| | | | | | |
|---|---|---|---|---|---|
| 2,796,903 | A * | 6/1957 | Gazelle | A61F 7/103 | |
| | | | | 607/109 | |
| 4,753,241 | A * | 6/1988 | Brannigan | A61F 7/02 | |
| | | | | 62/530 | |
| 5,119,812 | A * | 6/1992 | Angelo | A61F 7/02 | |
| | | | | 607/109 | |
| 5,628,772 | A * | 5/1997 | Russell | A61H 15/00 | |
| | | | | 601/115 | |
| D432,657 | S * | 10/2000 | Haynes | D24/208 | |
| 6,241,711 | B1 * | 6/2001 | Weissberg | A61F 7/10 | |
| | | | | 604/303 | |
| D668,703 | S * | 10/2012 | Gordon | D16/301 | |
| 10,406,035 | B1 * | 9/2019 | Scott | A61F 9/04 | |
| 2003/0014096 | A1 * | 1/2003 | Burkhart | A61F 9/04 | |
| | | | | 607/109 | |
| 2006/0036305 | A1 * | 2/2006 | Koby | A61F 7/02 | |
| | | | | 607/114 | |

(Continued)

*Primary Examiner* — Bradford C. Blaise
(74) *Attorney, Agent, or Firm* — Beckman Law P.C.; Christopher Beckman

(57) ABSTRACT

New forms of weighted and cooling sleep masks, and methods for their manufacturing and use, are provided. In some embodiments, a weighted sleep mask includes a plurality of interior chambers, loaded with cooling pieces, in unique arrangements. Such cooling pieces include material(s) with a relatively high density and cooling capacity, including materials with relatively high specific heat, such as stone or recycled glass. The cooling pieces may be at least partially enveloped with an insulating material. The plurality of interior chambers may be positioned in an array to cover, cool and press against and cool particular regions of the face, such as pressure points, and the eyes. A plurality of channels may run between the plurality of chambers, permitting the mask to conform with and exhaust heat and vapor at or about other areas of the face.

20 Claims, 9 Drawing Sheets

(56) References Cited

U.S. PATENT DOCUMENTS

| | | | | |
|---|---|---|---|---|
| 2007/0225782 | A1* | 9/2007 | Taylor | A61F 7/10 607/108 |
| 2008/0148769 | A1* | 6/2008 | Higgins | A61F 7/02 62/530 |
| 2014/0288624 | A1* | 9/2014 | Wasko | A61F 7/02 607/109 |
| 2016/0051404 | A1* | 2/2016 | Choucair | A61F 7/10 607/114 |
| 2017/0020767 | A1* | 1/2017 | DeMarie | A61H 7/001 |
| 2017/0027744 | A1* | 2/2017 | Floyd | A61F 7/106 |
| 2018/0008468 | A1* | 1/2018 | Bamberg | A61F 9/04 |
| 2020/0281770 | A1* | 9/2020 | Moreno | A41D 13/1184 |
| 2021/0045922 | A1* | 2/2021 | Lockett | A61F 11/12 |
| 2021/0059860 | A1* | 3/2021 | Alary | A61K 9/7007 |
| 2021/0267793 | A1* | 9/2021 | Bruder | A61F 7/03 |
| 2023/0017250 | A1* | 1/2023 | Seidenfeld | A61M 21/00 |
| 2024/0115424 | A1* | 4/2024 | Oliver | A61F 9/04 |

* cited by examiner

WEIGHTED, COOLING SLEEP MASK

FIELD OF THE INVENTION

The present invention relates to the fields of apparel and fashion accessories, and their methods of construction and use. More specifically, the present application relates to blindfolds and other masks for covering the eyes during sleep.

BACKGROUND

In some form, blindfolds have been in use at least for hundreds of years. Sleep masks are a form of blindfold intended for blocking out ambient light, to enhance sleep. Most likely to avoid unseen dangers at night, human beings evolved a diurnal circadian rhythm, in which they are alert during the daylight hours, and become drowsy in the evening, sleeping through the night. Ambient light is the primary time signal (a.k.a. "zeitgeber") for the human circadian rhythm and, as a result, it has been known for some time that unnatural light can interfere with sleep and sleep quality. In the presence of too much ambient light during the evening hours, the pineal gland in the human body creates less melatonin, making sleep more difficult. Although the mechanism was not yet understood, it was known at least as early as the 1900's that excessive ambient light, such as electric light can disrupt the sleep cycle.

In 1930, Elsie and Edward Hemphill, a married couple from San Francisco, developed a sleep mask entitled a "Sleep Eye Shade," culminating in U.S. Pat. No. 1,924,315. The Hemphill's invention was featured in the May, 1931 issue of Popular Science, and featured a blindfold that tightly sealed out ambient light, with pads in the lower/nose area, loops extending over and under the ears, and an adjustable band attached to the loops.

In recent years, sleep masks have grown in popularity. Increasing air travel, brighter urban living environments with ever more forms of electric lights, and increasingly unconventional work hours, have increased the need to eliminate ambient light, and enhance sleep. As a result, a number of sleep masks have been introduced onto the market, similar in nature to the mask first created by the Hemphills.

In addition, a wide variety of sleep-enhancing bedding products have been introduced, including several blankets incorporating weights. Weighted blankets are sometimes thought to enhance sleep by easing anxiety, at least for some users and in some instances.

There is a need for more effective sleeping masks, and, more specifically, sleeping masks that are comfortable, easy to use, and more effective at shutting out ambient light.

It should be understood that the disclosures in this application related to the background of the invention, in, but not limited to this section titled "Background," do not necessarily set forth prior art or other known aspects exclusively, and may instead include art that was invented concurrently or after the present invention and conception, and details of the inventor's own discoveries and work and work results.

SUMMARY OF THE INVENTION

New forms of weighted and cooling sleep masks, and methods for their manufacturing and use, are provided. In some embodiments, a weighted, cooling sleep mask includes a plurality of interior chambers, loaded with cooling pieces. In some embodiments, at least some of the cooling pieces are also weights, including materials with a density greater than fabrics and cushioning materials conventionally used in blindfolds and sleep masks. Such cooling pieces include material(s) with a relatively high density and cooling capacity, in some embodiments. For example, at least some such material(s) may have a relatively high specific heat, such as glass, stone, sand, ceramics, granite, water, aluminum, some other metals and alloys (e.g., steel, magnesium), salts, and plastics (e.g., polyethylene). In some embodiments, which are preferred, such material(s) have an especially high specific heat, such as water, glass and some stones, such as soapstone. Preferably, such materials also have especially good thermal conductivity, in some embodiments, including such materials (e.g., soapstone, marble, basalt, and steel). Even more preferably, such materials have a higher density, to apply weight to a user's face and in particular areas thereof (e.g., the eyes and/or temples), for reasons that will be discussed in greater detail below. Also preferably, such materials have a low or otherwise more beneficial environmental impact than other available options. For example, in some embodiments, such materials include bioplastics and/or materials created from plants, such as algae. In some embodiments, such materials include one or more polymers derived from plants. For example, in one embodiment, each such cooling piece includes a polymer outer layer, surrounding a freezable aqueous solution (i.e., a solution including water).

In some embodiments, such materials include a porous material and/or structure (e.g., lava stones, clays and sands), and may be filled or otherwise treated with a health-enhancing substance, such as essential oil, vitamin E, aloe vera, and moisturizers. In some embodiments, such porous materials may be filled or otherwise treated with a pleasant-smelling substance, such as a fragrance, essential oil, terpenes, and/or fragrance oil. In some embodiments, other materials, such as a fill material or porous panel or insert (e.g., made from a textile) may be otherwise included within the sleep mask, and may be sprayed or otherwise treated with such a health-enhancing and/or pleasant-smelling substance, serving as a substrate and diffuser of such a substance. In some embodiments, such a panel or insert may be removed and replaced from a specialized diffusion chamber, within the sleep mask.

In some embodiments, the cooling pieces are spherical or otherwise rounded. In some embodiments, however, the cooling pieces may have a non-rounded or semi-rounded shape. The cooling pieces may be at least partially enveloped with an insulating material. The plurality of interior chambers may be positioned in an array to cover, press against and cool particular regions of the face, such as pressure points, and the eyes. A plurality of channels may run between the plurality of chambers, permitting the mask to conform with and exhaust heat and vapor at or about other areas of the face, in some embodiments. The plurality of interior chambers may be constructed with a knit fabric, rather than a woven fabric, or an elastic, or relatively elastic fabric or other material, e.g., formed by stitching one or more interior panels of such a fabric. The sleep masks may also include a shaped insulation barrier, protecting the plurality of chambers from external heat transfer in certain areas, while encouraging heat transfer (i.e., cooling the user's face) in other regions. In some embodiments, such an insulation barrier, or another internal structure of such a sleep mask, may serve as an internal padding structure. For example, in some embodiments, such an internal padding structure may include polyester. As another example, in some embodiments, in some such embodiments, such an internal padding structure may include DACRON. In some embodiments, such an internal padding structure may include a layer that reflects thermal energy and, especially, in an outward direction (away from a user's face, when the weighted, cooling sleep mask is donned). In some embodiments, the cooling pieces may be at least partially enveloped with an insulating material.

In some embodiments, weighted, cooling sleep masks set forth in the present application have a weight that is far heavier than conventional blindfolds and sleep masks. For example, in some embodiments, weighted, cooling sleep masks set forth in the present application have a total weight at or exceeding 9 ounces. As another example, in some embodiments, weighted, cooling sleep masks set forth in the present application have a total weight at or exceeding 4 ounces. In some preferred embodiments, weighted, cooling sleep masks set forth in the present application have a total weight of between 10 and 12 ounces.

Where any term is set forth in a sentence, clause or statement ("statement"), each possible meaning, significance and/or sense of any term used in this application should be read as if separately, conjunctively and/or alternatively set forth in additional statements, as necessary to exhaust the possible meanings of each such term and each such statement.

It should also be understood that, for convenience and readability, this application may set forth particular pronouns and other linguistic qualifiers of various specific gender and number, but, where this occurs, all other logically possible gender and number alternatives should also be read in as both conjunctive and alternative statements, as if equally, separately set forth therein.

These and other aspects of the invention will be made clearer below, in other parts of this application. This Summary, the Abstract, and other parts of the application, are for ease of understanding only, and no part of this application should be read to limit the scope of the invention, whether or not it references matter in any other part.

BRIEF DESCRIPTION OF THE DRAWINGS

The features and advantages of the example embodiments of the invention presented herein will become more apparent from the detailed description set forth below when taken in conjunction with the following drawings.

DETAILED DESCRIPTION OF THE INVENTION

The example embodiments of the invention presented herein are directed to new forms of weighted and cooling sleep masks, and methods for their manufacturing and use, which are now described herein. This description is not intended to limit the application to the embodiments presented herein, which are only examples of the virtually unlimited possible embodiments falling within the scope of the present application. In fact, after reading the following description, it will be apparent to one skilled in the relevant art(s) how to implement the following example embodiments in alternative embodiments, including any possible order, number or other arrangement of components and sub-components (the following order, components, subcomponents and/or relationships being non-limiting).

Figure 1:
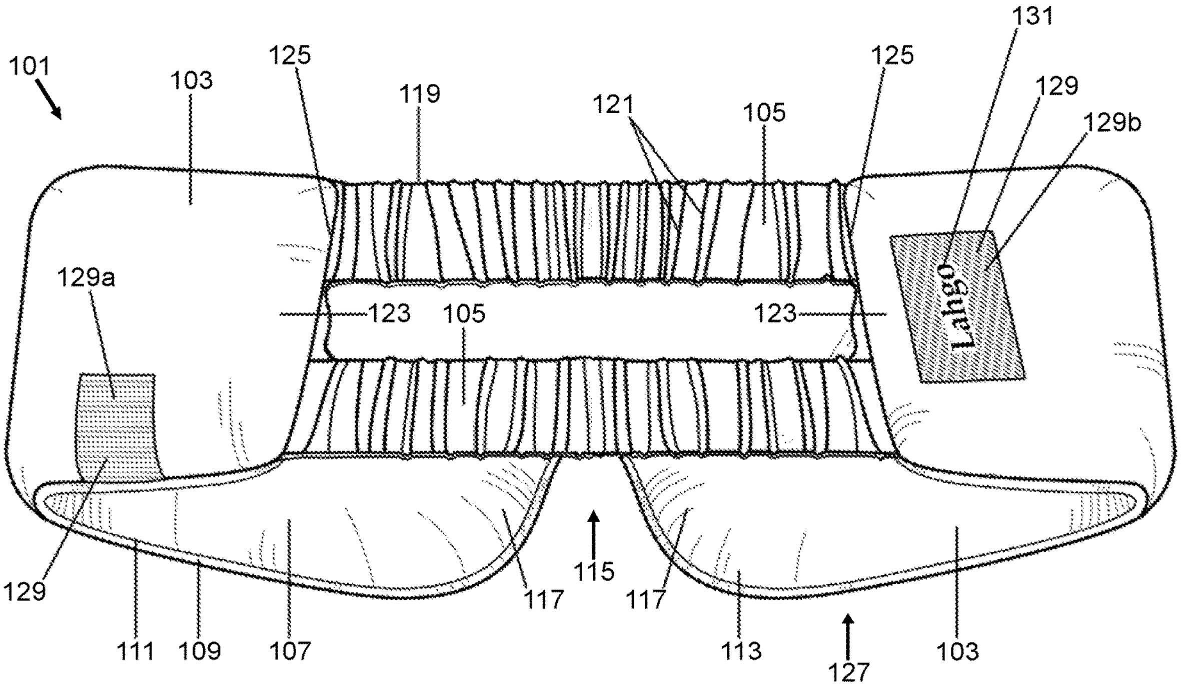
FIG. 1 is a back view of an example weighted, cooling sleep mask, including a head-wrapping eye shield, filled with cooling pieces, and incorporating multiple elastic headbands, in accordance with aspects of the present invention.

FIG. 1 is a back view of an example weighted, cooling sleep mask 101, including a head-wrapping eye shield 103, filled with cooling pieces (such cooling pieces not being pictured in the present figure), and incorporating multiple elastic headbands 105, in accordance with aspects of the present invention. Generally speaking, in some embodiments, sleep mask 101 and eye shield 103 may be constructed from one or more fabric panels serving as an outer housing of the sleep mask 101, such as example inward-facing exterior panel 107 and example outward-facing exterior panel 109. In some embodiments, either or both of exterior panel 107 and exterior panel 109 includes a flexible, soft, compliant material, preferably including silk. In some embodiments, such a material is only, or substantially only, silk. For example, in some embodiments, such a material includes a washable silk. In some embodiments, such a material is only, or substantially only, a washable silk. As another example of such a material, in some embodiments, such a material includes cotton, such as pima cotton. As another example of such a material, in some embodiments, such a material is a blend. As another example of such a material, in some embodiments, such a material includes polyester. In some embodiments, such a flexible, soft, compliant material is included, at least, on exterior panel 107, thus on an inward-facing side of eye shield 103 (i.e., facing the user's face when donned). In some embodiments, either or both of exterior panel 107 and exterior panel 109 may each be constructed of multiple yarns, plies or layers of fabric. In some embodiments, exterior panel 107 and exterior panel 109 may be fastened together (e.g., in various embodiments, by stitching, bonding, stapling, fabric glue, fusing methods, or a fastener, such as a zipper or VELCRO) at a seam, such as example seam 111.

In some embodiments, as a result of the filling of eye shield 103 with cooling pieces, eye shield 103 has a 3-dimensionally rounded outer profile, especially along its edges facing inward (toward the user's face), such as at example rounded interior edge 113, increasing comfort for a user. Although the cooling pieces filling eye shield 103 are not yet pictured in the present figure, it should be understood that, in some embodiments, such cooling pieces may fill an interior space within eye shield 103, adding weight and increasing the tendency of eye shield 103 to press against, and conform with, the contours of a user's face, when sleep mask 101 is donned.

In some embodiments, discussed in greater detail below, such a weighted sleep mask includes a plurality of interior chambers, loaded with such cooling pieces, each chamber maintaining a general positioning and apportionment of cooling pieces at or about certain regions of the sleep mask 101. Such regions of the sleep mask 101, and their relative positioning near corresponding areas of a user's face, are discussed in greater detail, below.

Among other aspects of sleep mask 101 demonstrated in the present figure, in some embodiments, a rounded nose notch 115, for accommodating a user's nose when sleep mask 101 is donned, is included. Unlike other sleep masks, however, rounded nose notch 115 is substantially filled with cooling pieces, in some embodiments, and, in some such embodiments, held on or about nose notch regions 117, by one or more of the plurality of interior chambers (again, not pictured in the present figure, but set forth in greater detail below).

In some embodiments, the multiple elastic headbands 105 may each include a flattened, elastomeric band, which may stretch and elongate, and relax and rebound, within a limited range (i.e., a maximum and minimum length). In some embodiments, the maximum length of each such elastomeric band, and multiple elastic headbands 105, is enforced by a strong, stiff, encasing material, such as example encasing material 119, which, when such an elastomeric band is relaxed and at a minimum length (not stretched), becomes folded into pleats, such as example pleats 121. In some embodiments, such an encasing material includes silk. In some embodiments, such an encasing material is silk. In some embodiments, such an encasing material includes cotton. However, when stretched, each of the elastomeric bands (one each in each of headbands 105) is stretched, pleats 121 are unfolded as the encasing material 119, and each of headbands 105 as a result, extends to a maximum length (not pictured, but, in some embodiments, at or about approximately 60-70% longer than the minimum length, in some embodiments). In some embodiments, such a maximum length is at or about 65% longer than such a minimum length. In some embodiments, such a maximum length is at or about 64% longer than such a minimum length. In some embodiments, such a maximum length is at or about 50% longer than such a minimum length. In some embodiments, such a maximum length is at or about 80% longer than such a minimum length. However, in still other embodiments, such a maximum length is longer or shorter than such a minimum length, by a greater or lower relative amount than the above examples.

In various embodiments, headbands 105 may be attached to or integrated with wrapping ends 123 of eye shield 103, at junction areas, such as example junction areas 125. While a front portion 127 of eye shield 103 is positioned on or about a user's face when sleep mask 101 is donned, wrapping ends 123 may wrap about at least part of the sides and back of a user's head, when so donned.

In some embodiments, decorative panels, such as example decorative smaller panels 129, may be included, which may be stitched, bonded, stapled, glue, fused, fastened to, or integral with outward-facing exterior panel 109. In some embodiments, at least part of at least one of such decorative panels, such as example decorative smaller panels 129, may include a brand or other identifier. For example, in the present figure, the right-hand side example decorative smaller panel 129*b*, includes such a brand or other identifier 131. However, by contrast, left-hand side example decorative smaller panel 129*a*, may not depicted as including such a brand or other identifier (at least in a visible form). In some embodiments, such an identifier may indicate one of a plurality of sizes or appropriate user types for sleep mask 101, which may be provided in a plurality of such sizes or otherwise in a configuration for a particular user, or user type.

Figure 2:
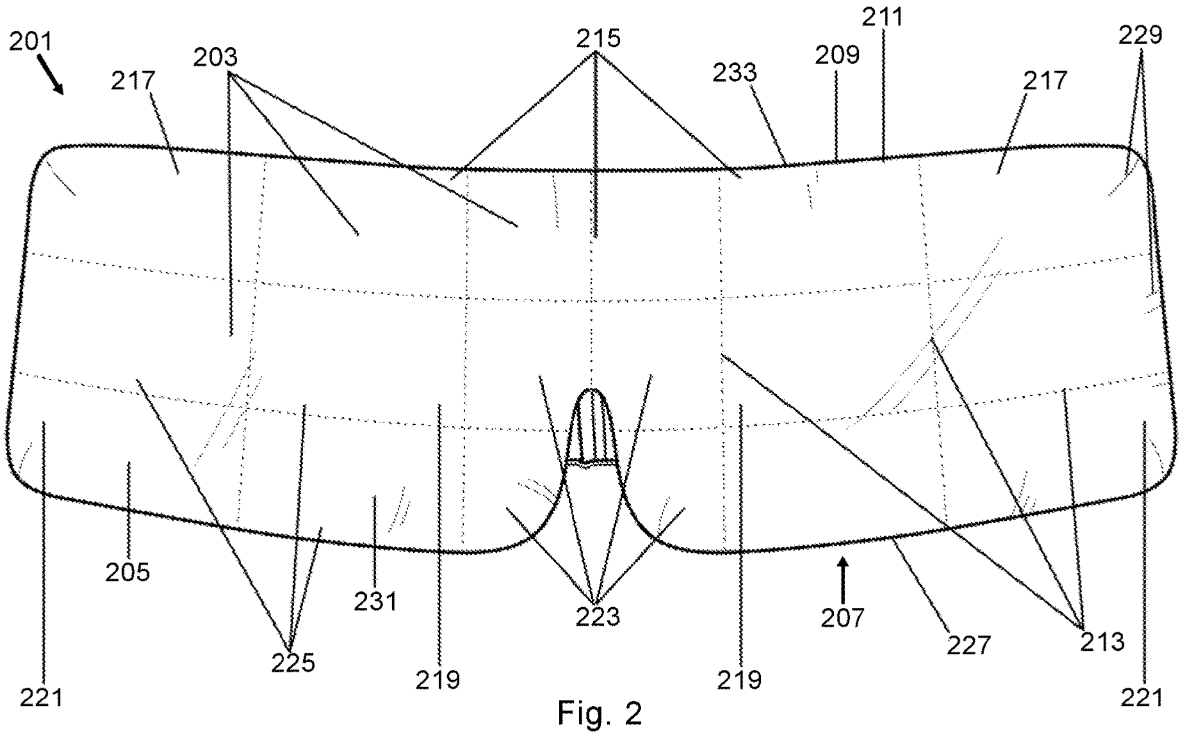
FIG. 2 is a front view of a similar example weighted, cooling sleep mask as discussed in reference to FIG. 1, above, illustrating additional aspects of the present invention.

FIG. 2 is a front view of another example weighted, cooling sleep mask 201, similar in nature to that discussed in reference to FIG. 1, above, illustrating additional aspects of the present invention. In at least some embodiments, cooling sleep mask 301 may include any or all of component(s), material(s) and structure(s) set forth above, with reference to cooling sleep mask 101, and with reference to weighted, cooling sleep masks set forth elsewhere in this application. In some embodiments, as mentioned above, such a sleep mask includes a plurality of interior chambers, loaded with cooling pieces (such cooling pieces not being pictured in the present figure), such as example interior chambers 203, which may be formed by stitching together two or more interior layers of fabric 205, held within a main body 207 of sleep mask 201. Such a main body 207 may be include a housing 209, formed by one or more exterior panel(s) 211, which may be, or be similar to, exterior panel 107 and exterior panel 109, discussed above, including the same, or similar material(s). In some embodiments, each of interior chambers 203 are the same or similar in size, and are filled with the same or a similar number, or the same or a similar amount in size or amount in weight, of such cooling pieces. In some embodiments, however, at least some of interior chambers 203 may differ from other interior chambers in size or capacity, and/or hold a different number and/or amount of cooling pieces than such other interior chambers.

In any event, in some embodiments, each of interior chambers 203 maintain a general positioning and apportionment of cooling pieces, which may be held within them by stitching or other attachment areas, such as example stitching or other attachment areas 213, (e.g., linear stitches, also creating space and air channels (a.k.a., air-filled voids) along their length), at or about certain regions of the sleep mask 201. Such regions of the sleep mask 201 ensure that the cooling and pressure-application properties of the cooling pieces are applied at corresponding areas on or about a user's face and head (e.g., pressure points, including higher concentrations of nerve endings on or about the skin in those areas), when sleep mask 201 is donned, in some embodiments. For example, interior chambers 215 tend to be applied to the forehead and brow areas of a user's face, when sleep mask 201 is donned. As another example, interior chambers 217 tend to be applied to the temples or upper side of the head, when sleep mask 201 is donned. As another example, interior chambers 219 tend to be applied to the user's cheeks, when sleep mask 201 is donned. As another example, interior chambers 221 tend to be applied to the lower side of the user's head and ears, when sleep mask 201 is donned. As yet another example, interior chambers 223 tend to be applied to the user's nasal area, when sleep mask 201 is donned. In some embodiments, any of the interior chambers are filled or otherwise treated with a health-enhancing substance, such as essential oil, vitamin E, aloe vera, and moisturizers. In some embodiments, any of the interior chambers may be filled or otherwise treated with a pleasant-smelling substance, such as a fragrance, essential oil, terpenes, and/or fragrance oil. However, preferably, in some embodiments, such a pleasant-smelling substance may be provided on or about interior chambers 223 specifically.

In some embodiments, suitable for a seated user, rather than a user laying on her or his back, the interior chambers are constructed with a greater stiffness, tightness and/or strength in their constituent materials (e.g., copper or other non-elastomeric fibers) at the lower side of each chamber (a.k.a., the "base" of each chamber, such as example chamber bases 225). As a result, the tendency of each chamber to sag and billow at each such base, as gravity pulls the cooling pieces downward, is counteracted by that stiffness, tightness and/or strength. In other embodiments, strands or cords (not pictured in the present figure) attached to and/or extending periodically from one interior wall, on one side, and the other interior wall, on the other side, of each chamber, may be included—especially on or about the base of each chamber.

In some embodiments, such stands or cords may be elastomeric, include a resilient elastomeric material, such as silicone or rubber. In some embodiments, such strands or cords include a strong, stiff material. In either of the two embodiments, immediately above, the strands or cords serve to counteract the tendency of the cooling pieces to pool at the base of each chamber, instead creating a more flattened outer profile for the grid formed by the plurality of interior chambers, and for the eye shield 227 of sleep mask 201 in which it is included.

In some embodiments, as also demonstrated with respect to sleep mask 101, above in reference to FIG. 1, sleep mask 201 exhibits a rounded outer profile, as shown by example rounded shading lines 229. Such a rounded outer profile may be caused, at least in part, by the cooling pieces filling sleep mask 201, in some embodiments. In some embodiments, such a rounded outer profile may also be caused, at least in part, by an insulating, cushioning filler (such as DACRON), which may be formed to resist the exchange of heat from a front side 231 or side edges, such as example side edge 233, of sleep mask 201. In some embodiments, such an insulating, cushioning filler may be omitted, or reduced in amount, on an inward-facing side (facing the user's face when donned) of sleep mask 201, encouraging the diffusion of heat energy from the user's face, and into the cooling pieces.

Figure 3:
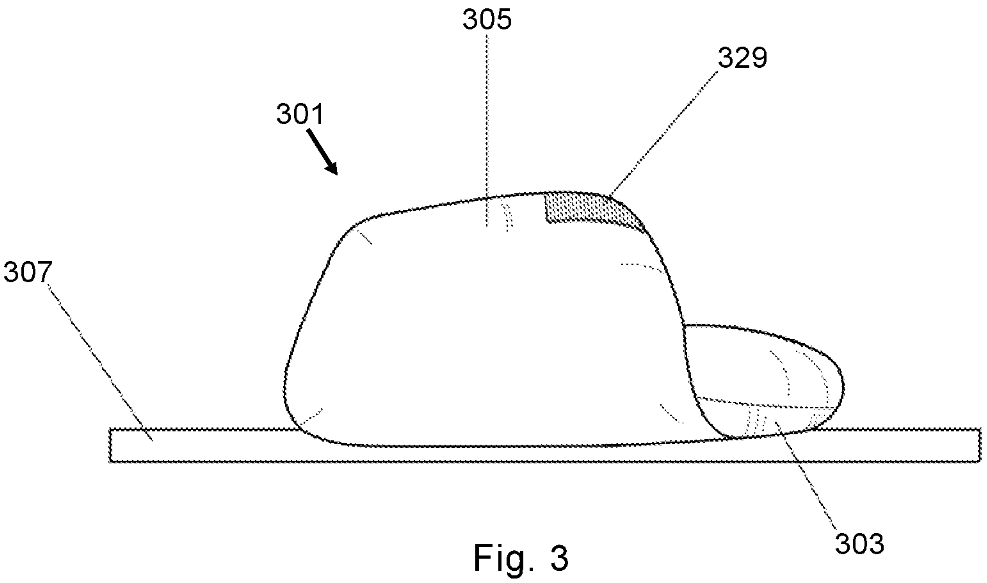
FIG. 3 is a left-hand side view of a similar example weighted, cooling sleep mask as discussed in reference to FIGS. 1 and 2, above, illustrating additional aspects of the present invention.

FIG. 3 is a left-hand side view (from the perspective of a user wearing it) of a similar example weighted, cooling sleep mask 301, as that discussed in reference to FIGS. 1 and 2, above, illustrating additional aspects of the present invention. In at least some embodiments, cooling sleep mask 301 may include any or all of component(s), material(s) and structure(s) set forth above, with reference to cooling sleep mask 101 and cooling sleep mask 201, and with reference to weighted, cooling sleep masks set forth elsewhere in this application. Included in cooling sleep mask 301 are example head-wrapping eye-shield 303, which comprises wrapping ends, including example wrapping end 305, (configured to be wrap over a user's ears and sides of the head, in some embodiments). In some embodiments, cooling sleep mask 301, and, in some embodiments, its wrapping ends, such as example wrapping end 305, in particular, include a sound-attenuating material, which may be in an interior portion of wrapping ends such as example wrapping end 305. In some embodiments, such a sound-attenuating material may include an acoustic foam or other stuffing or baffling known in the art for attenuating noise, and suitable for inclusion in fashion accessories and wearables. In such embodiments, when wrapped on or about a user's ears, cooling sleep mask 301 and/or wrapping ends such as example wrapping end 305 may serve to decrease ambient noise experienced by the user, making rest and sleep more practical. However, in some embodiments, such a wrapping end(s), or other structures configured to cover a user's ears, are not included. In some such embodiments, a shorter eye shield, with shorter or omitted wrapping ends, may cover only the eyes of a user when cooling sleep mask 501 is donned, or may cover an area adjacent to the user's eyes, such as the temples, cheeks, and or side of the head, without covering the ears (or, in some embodiments, without completely covering the ears).

It should be understood that, because cooling sleep mask 301 comprises flexible, compliant materials, such as silk and other compliant fabrics, and stretchable internal components, such as internal chambers holding cooling pieces with foldable areas, along lines of stitching (not pictured in the present figure), it is highly conforming and foldable. Thus, cooling sleep mask 301 is shown in a folded, and somewhat flattened configuration, under the force of gravity onto a flat surface 307 on which it has been placed, as pictured, in FIG. 3.

Figure 7:
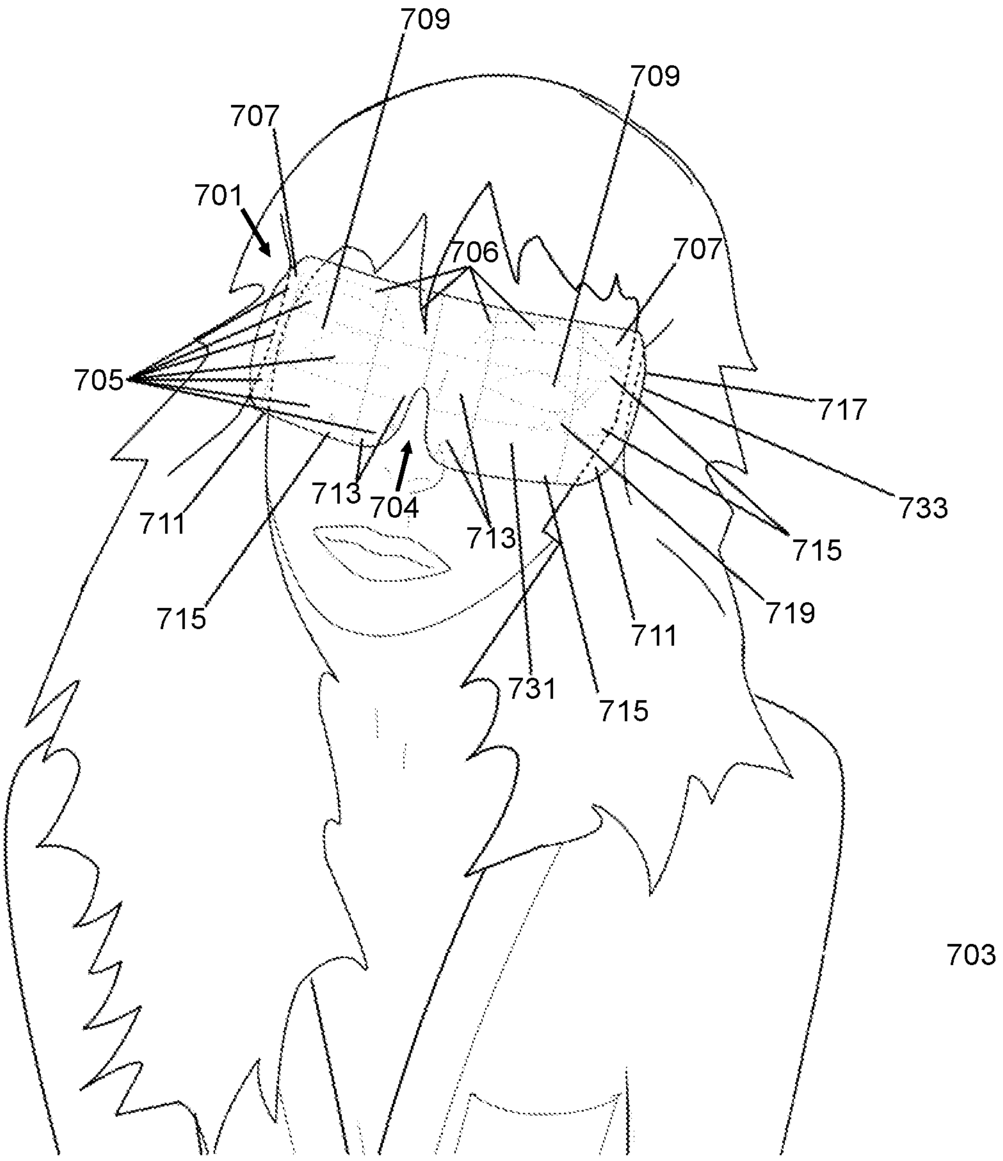
FIG. 7 is a perspective drawing of a similar example weighted, cooling sleep mask as discussed in reference to FIGS. 1-6, above, and a user who is wearing it, in accordance with aspects of the present invention.

However, when donned over a user's face and head, as shown, for example, in FIG. 7, such a cooling sleep mask conforms readily to all of the contours of a user's face and head, as is discussed in greater detail elsewhere in this application. In other words, weighted sleep masks set forth in the present application take on different conformations, in 3-dimensional space, when stored and when worn by a user. When hung, or as discussed above, when placed on a flat surface, cooling sleep mask 301 takes on a more folded, flattened 3-dimensional shape, overall, in which the eye shield 303 may contact wrapping end 305 and elastic headbands (not visible in the present figure, but similar in nature to elastic headbands 105) with very little open space between those structures. When unfolded, and donned (placed onto a human head), over the eyes, however, cooling sleep mask 301 takes on a more rounded 3-dimensional shape, with ample space between eye shield 303, wrapping end 305 and such elastic headbands. This latter 3-dimensional conformation, and methods of wearing such a cooling sleep mask, will be discussed in greater detail below, in reference to FIG. 7.

Also visible in the present figure is an example decorative panel 329, which may be similar in nature to the left-hand side example decorative panel 129*a* set forth in FIG. 1. In at least some embodiments decorative panel 329 may also serve as a support, handle and/or guard, to reduce damage to the remainder of cooling sleep mask 301, such as damage from abrasion, and/or increasing a user's grip (when used as a handle). In some embodiments, example decorative panel 329 may serve as an anchor, for anchoring a tag, or string or cord holding a tag, or other attachment (e.g., a temporary price tag).

Figure 4:
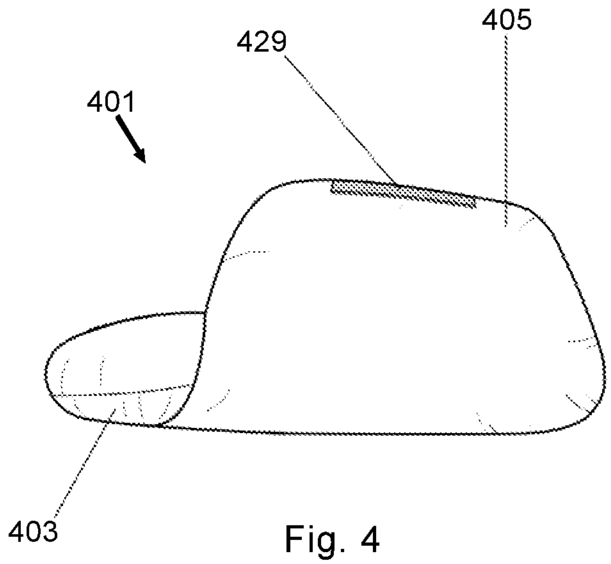
FIG. 4 is a right-hand side view of a similar example weighted, cooling sleep mask as discussed in reference to FIGS. 1-3, above, illustrating additional aspects of the present invention.

FIG. 4 is a right-hand side view (again, from the perspective of a user wearing it) of a similar example weighted, cooling sleep mask 401, as that discussed in reference to FIGS. 1-3, above, illustrating additional aspects of the present invention. In at least some embodiments, cooling sleep mask 401 may include any or all of component(s), material(s) and structure(s) set forth above, with reference to cooling sleep mask 101, cooling sleep mask 201 and cooling sleep mask 301, and with reference to weighted, cooling sleep masks set forth elsewhere in this application. Thus, and again visible in the present figure, is a head-wrapping eye-shield, now shown as example eye shield 403, which comprises wrapping ends, such as example wrapping end 405. As discussed above, wrapping ends, such as example wrapping end 405, are configured to be wrap over a user's ears and sides of the head, in some embodiments. However, in some embodiments, such a wrapping end(s), or other structures configured to cover a user's ears, are not included. In some such embodiments, a shorter eye shield, with shorter or omitted wrapping ends, may cover only the eyes of a user when cooling sleep mask 501 is donned, or may cover an area adjacent to the user's eyes, such as the temples, cheeks, and or side of the head, without covering the ears (or, in some embodiments, without completely covering the ears).

Visible in the present figure is an example decorative panel 429, which may be similar in nature to the right-hand side example decorative panel 129*b*, set forth in FIG. 1. In at least some embodiments decorative panel 429 may also serve as a support, hanging loop and/or guard, to reduce damage to the remainder of cooling sleep mask 401, such as damage from abrasion.

Figure 5:
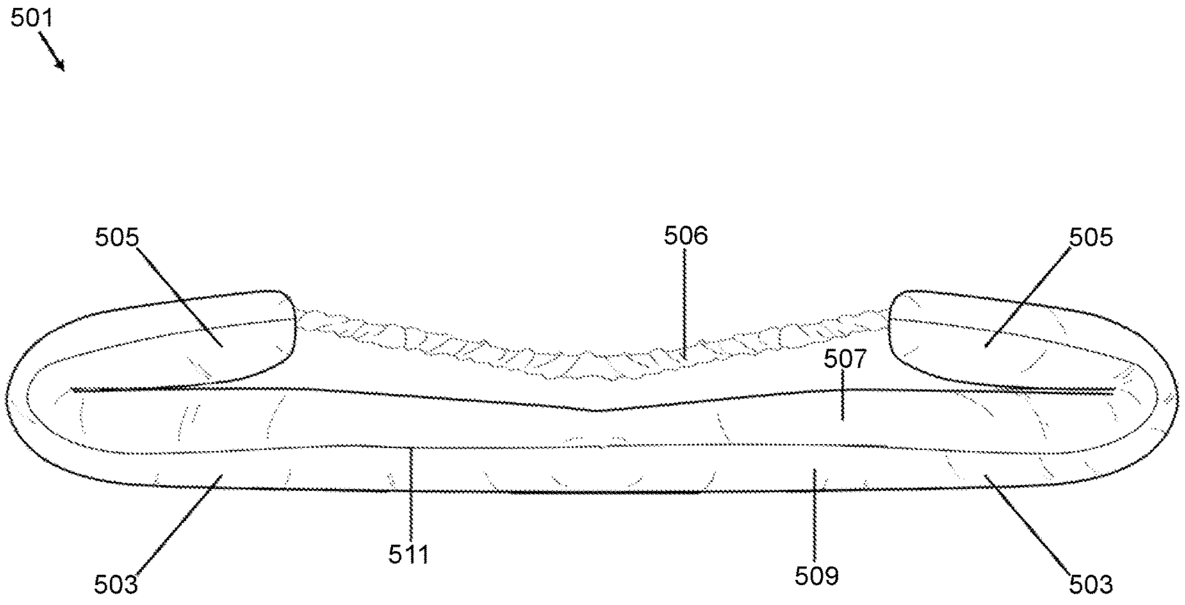
FIG. 5 is a top view of a similar example weighted, cooling sleep mask as discussed in reference to FIGS. 1-4, above, illustrating additional aspects of the present invention.

FIG. 5 is a top view of a similar example weighted, cooling sleep mask 501 as that discussed in reference to FIGS. 1-4, above, illustrating additional aspects of the present invention. In at least some embodiments, cooling sleep mask 501 may include any or all of component(s), material(s) and structure(s) set forth above, with reference to cooling sleep mask 101, cooling sleep mask 201, cooling sleep mask 301, and cooling sleep mask 401, and with reference to weighted, cooling sleep masks set forth elsewhere in this application. Thus, and again visible in the present figure, is a head-wrapping eye-shield, now shown as example eye shield 503, which comprises wrapping ends, such as example wrapping ends 505, which, when donned, may be portions that wrap about and cover at least part of the user's head. As discussed above, wrapping ends, such as example wrapping ends 505, are configured to be wrapped over a user's ears and sides of the head, in some embodiments. However, in some embodiments, such wrapping ends, or other structures configured to cover a user's ears, are not included. In some such embodiments, a shorter eye shield, with shorter or omitted wrapping ends, may cover only the eyes of a user when cooling sleep mask 501 is donned, or may cover an area adjacent to the user's eyes, such as the temples, cheeks, and or side of the head, without covering the ears (or, in some embodiments, without completely covering the ears). In some such embodiments, multiple elastic headbands, such as example elastic headband 506 (a second headband not being visible in the present figure), which may be similar in nature to any of the elastic headbands set forth elsewhere in the present application, are provided. In some such embodiments, each such headband may be configured, e.g., being adequately spaced from one another, to lay above and below a user's ear. However, in some embodiments, by contrast, each such headband may be configured, e.g., being spaced close enough to another headband, or even abutting another headband, to lay over a user's ears, holding them tightly against the user's head.

As with other example weighted and cooling sleep masks set forth in the present application, cooling sleep mask 501 and eye shield 503 may be constructed from one or more fabric panels serving as an outer housing of the sleep mask 501, such as example inward-facing exterior panel 507 and example outward-facing exterior panel 509, in some embodiments. In some embodiments, either or both of inward-facing exterior panel 507 and outward-facing exterior panel 509 include(s) a flexible, soft, compliant material. In some embodiments, such a flexible, soft, compliant material is included on inward-facing exterior panel 507, thus on an inward-facing side of eye shield 503 (i.e., facing the user's face when donned). In some embodiments, such a flexible, soft, compliant material is included on outward-facing exterior panel 509, thus on an outward-facing side of eye shield 503 (i.e., facing away from a user's face when donned). For example, in some embodiments, either or both of inward-facing exterior panel 507 and outward-facing exterior panel 509 include(s) silk. In some embodiments, either or both of inward-facing exterior panel 507 and outward-facing exterior panel 509 are 100% silk. In some embodiments, either or both of inward-facing exterior panel 507 and outward-facing exterior panel 509 include(s) include washable silk. In some embodiments, either or both of inward-facing exterior panel 507 and outward-facing exterior panel 509 include(s) include silk charmeuse. In some embodiments, either or both of inward-facing exterior panel 507 and outward-facing exterior panel 509 include(s) include materials that have been subjected to a texturizing process. For example, in some embodiments, such a process is a sand wash process.

In some embodiments, inward-facing exterior panel 507 and example outward-facing exterior panel 509 include at least some different materials, in comparison to one another. For example, in some embodiments, inward-facing exterior panel 507 includes a material suitable for a lining, such as linings in contact with human skin, while outward-facing exterior panel 509 does not include such a material. In some embodiments, such a lining material includes Rayon. In some embodiments, such a lining material includes elastane. In some embodiments, such a lining material is 95% rayon and 5% elastane. In some embodiments, such a lining material may be used as a lining in another part or location of the weighted, cooling sleep mask, or a carrying bag, e.g., lining an interior of a pocket large enough, and with a complementary size to accommodate, the weighted, cooling sleep mask (at least when folded in half, lengthwise). An example embodiment of such a carrying bag is provided as FIG. 11, discussed below.

In some embodiments, either or both of inward-facing exterior panel 507 and outward-facing exterior panel 509 may each be constructed of multiple yarns, plies or layers of fabric. In some embodiments, inward-facing exterior panel 507 and outward-facing exterior panel 509 may be fastened together (e.g., in various embodiments, by stitching, bonding, stapling, fabric glue, fusing methods, or a fastener, such as a zipper or VELCRO) at a seam, such as example seam 511. In some embodiments, a visible seam such as example seam 511 may be omitted, and the weighted, cooling sleep mask may instead have a single, fused exterior panel (not pictured), surrounding the exterior of eye shield 503. In some such embodiments, inward-facing exterior panel 507 and outward-facing exterior panel 509 may be seamlessly fused together, or otherwise may be comprised in a single piece of material.

Figure 6:
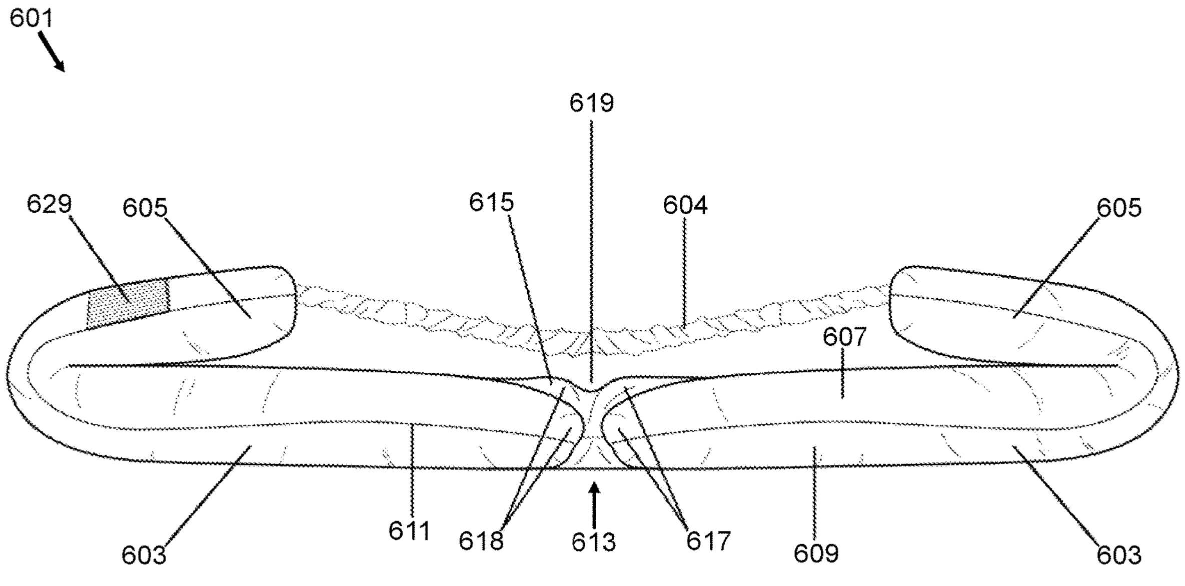
FIG. 6 is a bottom view of a similar example weighted, cooling sleep mask as discussed in reference to FIGS. 1-5, above, illustrating additional aspects of the present invention.

FIG. 6 is a bottom view of a similar example weighted, cooling sleep mask 601 as that discussed in reference to FIGS. 1-5, above, illustrating additional aspects of the present invention. In at least some embodiments, cooling sleep mask 501 may include any or all of component(s), material(s) and structure(s) set forth above, with reference to cooling sleep mask 101, cooling sleep mask 201, cooling sleep mask 301, and cooling sleep mask 401, and with reference to weighted, cooling sleep masks set forth elsewhere in this application. Thus, and again visible in the present figure, is a head-wrapping eye-shield, now shown as example eye shield 603, which comprises wrapping ends, such as example wrapping ends 605, which, when donned, may be portions that wrap about and cover at least part of the user's head. As discussed above, wrapping ends, such as example wrapping ends 605, are configured to be wrapped over a user's ears and sides of the head, in some embodiments.

As discussed above, in some such embodiments of weighted, cooling sleep masks in accordance with aspects set forth in this application, multiple elastic headbands, such as two elastic head bands, may be used. For example, as pictured in FIG. 5, and discussed above, one such example elastic headband 506 (not visible in the present figure) is located in a lower position, and visible from the bottom view perspective of that figure, in some embodiments, and a second example elastic headband, such as example elastic headband 604, located in a higher position than example elastic headband 506, is provided, and visible from the top view perspective of the present figure (FIG. 6) in some embodiments. As discussed above, each or all of such elastic headbands may be similar in nature to any of the elastic headbands set forth elsewhere in the present application. As discussed elsewhere in this application, in some embodiments, such multiple elastic headbands may each include a flattened, elastomeric band, which may stretch and elongate, and relax and rebound, within a limited range (i.e., a maximum and minimum length), in some embodiments. For example, in some embodiments, may be include a flat elastic ribbon between, or approximately between, 0.5 and 1.5 inches in height (e.g., 1 inch in height), measured from top to bottom, in the perspectives of FIGS. 5 and 6. Although, as discussed above, such multiple elastic headbands may be provided, in some embodiments, they may be covered with a single outer sheet of material, such as the strong, stiff, encasing materials for headbands discussed above, creating, at least in appearance, a single headband. As discussed above, such strong, stiff, encasing materials, or other length-limiting devices, may enforce a maximum length (fully stretched) of such multiple elastic headbands, in some embodiments, at or about approximately 60-70% longer than the minimum length, in some embodiments. In some embodiments, such a maximum length is at or about 65% longer than such a minimum length. In some embodiments, such a maximum length is at or about 64% longer than such a minimum length. In some embodiments, such a maximum length is at or about 50% longer than such a minimum length. In some embodiments, such a maximum length is at or about 80% longer than such a minimum length. However, in still other embodiments, such a maximum length is longer or shorter than such a minimum length, by a greater or lower relative amount than the examples provided above.

As with other example weighted and cooling sleep masks set forth in the present application, cooling sleep mask 501 and eye shield 503 may be constructed from one or more fabric panels serving as an outer housing of the sleep mask 501, such as example inward-facing exterior panel 607 and example outward-facing exterior panel 609, in some embodiments, any or all of which may include any of the materials set forth in this application or known in the art for any fabric panel and, especially, for such fabric panels. In some embodiments, inward-facing exterior panel 607 and outward-facing exterior panel 609 may be fastened together (e.g., in various embodiments, by stitching, bonding, stapling, fabric glue, fusing methods, or a fastener, such as a zipper or VELCRO) at a seam, such as example seam 611.

In some embodiments, weighted, cooling sleep masks in accordance with aspects set forth in this application, such as example weighted, cooling sleep mask 601, include a rounded nose notch, such as example rounded nose notch 613, for accommodating a user's nose when sleep mask 601 is donned. In some embodiments, rounded nose notch 613 is substantially filled with cooling pieces, in some embodiments, and, in some such embodiments, at least some of such cooling pieces are held on or about an enlarged and reinforced nose notch region(s), such as example enlarged and reinforced nose notch region 615, which faces and abuts a user's nasal area when donned, and are so held by one or more of the plurality of interior chambers (internal, but, in some embodiments, located at or about areas within enlarged and reinforced nose notch region 615, such as the areas shown as example interior chamber positions 617 and example interior chamber positions 618). As also discussed elsewhere in this application, in some embodiments, one or more air channels, such as example central air channel 619, which may be formed by stitching between such interior chambers, in some embodiments, are provided. In some embodiments, a user may fold weighted, cooling sleep mask 601 along that stitching and central air channel, folding weighted, cooling sleep mask 601 onto itself, forming four stacked layers, for stowing and travel (e.g., after placing weighted, cooling sleep mask 601 into a carrying bag, such as example carrying bag 1101, set forth below. Thus, as an example, if cooling, weighted sleep mask 601 has an overall length, when laid flat as pictured, of about 9 inches, as may be preferred for at least some (e.g., a women's sized) weighted, cooling sleep mask, when so folded, the mask will be approximately 4.5 (or slightly larger) in length. As another example, such a woman's sized sleep mask may have such an overall length of, or about, 8.8 inches, or slightly larger, in some embodiments and, when so folded in half, may have a length of, or about, 4.4 inches, or slightly larger. As another example, if cooling, weighted sleep mask 601 has an overall length of about 12 inches, as may be preferred for at least some (e.g., a men's sized) weighted, cooling sleep mask, when so folded, the mask will be approximately 6 inches (or slightly larger) in length.

FIG. 7 is a perspective drawing of a similar example weighted, cooling sleep mask 701 as discussed in reference to FIGS. 1-6, above, and a user 703 who is wearing it, in accordance with aspects of the present invention. As discussed elsewhere in this application, user 703 has donned sleep mask 701 (e.g., after chilling cooling pieces held within it) and by positioning weighted, cooling sleep mask 701 centrally on her face, which positioning in some embodiments, by placing her nose into and against a nose notch region 704, which may be, or may be similar to, nose notch region 615, discussed above. As a result, each of a plurality of interior chambers, such as the examples shown as interior chambers 705, which may be the same or similar to interior chambers set forth above, are positioned over different, discrete areas of a user's face and head. For example, in some embodiments, to ensure that the cooling and pressure-application properties of the cooling pieces are applied at corresponding areas on or about effective areas of user 703's face and head, each of such interior chambers may be positioned at or about pressure points of user 703's face and head, which are areas of the user 703's face having higher concentrations of nerve endings on or about the skin, when sleep mask 701 is donned, as pictured. For example, interior chambers 706 tend to be applied to the forehead and brow areas of a user's face, when sleep mask 701 is donned, as pictured. As another example, interior chambers 707 tend to be applied to the temples or upper side of the head, when sleep mask 701 is donned, as pictured. As another example, interior chambers 709 tend to be applied to the user's cheeks, when sleep mask 701 is donned, as pictured. As another example, interior chambers 711 tend to be applied to the lower side of the user's head and ears, when sleep mask 701 is donned, as pictured. As yet another example, interior chambers 713 tend to be applied to the user's nasal area, when sleep mask 701 is donned, as pictured. In some embodiments, any of the interior chambers are filled or otherwise treated with a health-enhancing substance, such as essential oil, vitamin E, aloe vera, and moisturizers. In some embodiments, any of the interior chambers may be filled or otherwise treated with a pleasant-smelling substance, such as a fragrance, essential oil, terpenes, and/or fragrance oil. However, preferably, in some embodiments, such a pleasant-smelling substance may be provided on or about interior chambers 223 specifically.

In some embodiments, the cooling pieces have a high specific heat, as discussed in this application, and therefore absorb heat energy from those different, discrete areas—especially if chilled, as also discussed in this application. In addition, because the cooling pieces have a high density, they apply weight and pressure against user 703's face, in those same regions, which may be beneficial for cosmetic reasons and result in acupressure therapy to pressure points on the human user's face, as discussed above, in some embodiments.

In some embodiments, suitable for a seated user, as pictured, rather than a user laying on her or his back, the interior chambers are constructed with a greater stiffness, tightness and/or strength in their constituent materials (e.g., copper or other non-elastomeric fibers) at the lower side of each chamber (a.k.a., the "base" of each chamber, such as example chamber bases 715). As a result, the tendency of each chamber to sag and billow at each such base, as gravity pulls the cooling pieces downward, is counteracted by that stiffness, tightness and/or strength. In other embodiments, strands or cords (not pictured in the present figure) attached to and/or extending periodically from one interior wall, on one side, and the other interior wall, on the other side, of each chamber, may be included—especially on or about the base of each chamber.

In some embodiments, such stands or cords may be elastomeric, include a resilient elastomeric material, such as silicone or rubber. In some embodiments, such strands or cords include a strong, stiff material. In either of the two embodiments, immediately above, the strands or cords serve to counteract the tendency of the cooling pieces to pool at the base of each chamber, instead creating a more flattened outer profile for the grid formed by the plurality of interior chambers, and for the eye shield 717 of sleep mask 201 in which it is included.

In some embodiments, as also demonstrated with respect to sleep mask 101, above in reference to FIG. 1, sleep mask 701 exhibits a rounded outer profile, as shown by example rounded shading lines 719. Such a rounded outer profile may be caused, at least in part, by the cooling pieces filling sleep mask 701, in some embodiments. In some embodiments, such a rounded outer profile may also be caused, at least in part, by an insulating, cushioning filler (such as DACRON), which may be formed to resist the exchange of heat from a front side 731 or side edges, such as example side edge 733, of sleep mask 701. In some embodiments, such an insulating, cushioning filler may be omitted, or reduced in amount, on an inward-facing side (facing the user's face when donned) of sleep mask 701, encouraging the diffusion of heat energy from the user's face, and into the cooling pieces.

Figure 8:
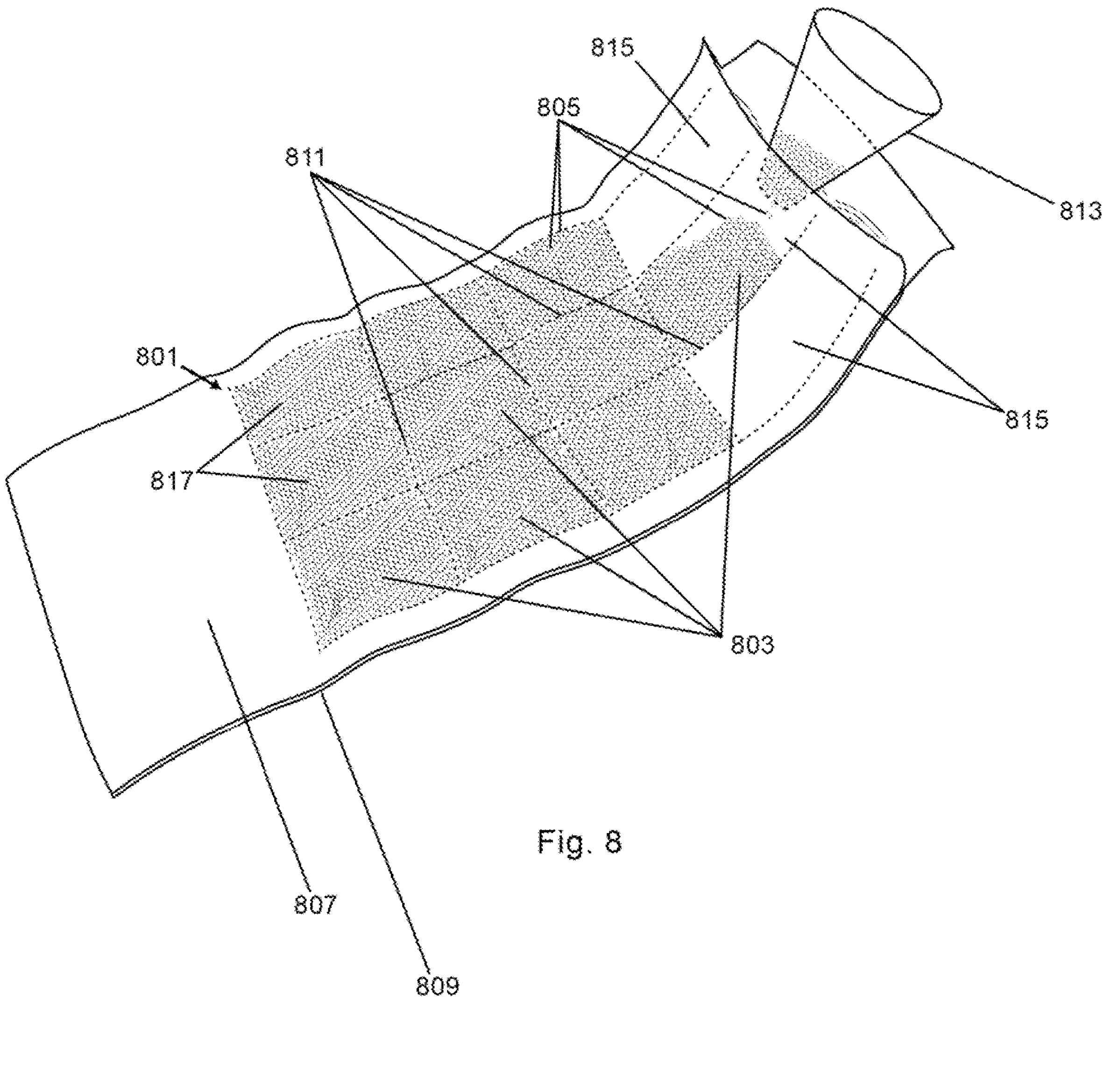
FIG. 8 is a perspective drawing of an example grid of interior chambers, being created and filled with example cooling pieces, in accordance with aspects of the present invention.

FIG. 8 is a perspective drawing of an example grid 801 of interior chambers, such as the example plurality of interior chambers shown, including example interior chambers 803, being created and filled with cooling pieces, such as example cooling pieces 805, which grid, interior chambers and/or cooling pieces may be attached to, inserted into and/or integrated with any of the sleep masks set forth in the present application, as discussed herein, thereby providing a weighting and heat transfer (cooling) device to enhance sleep.

As discussed above, in some embodiments, such a grid, and such interior chambers, may be constructed from one or more panels or plies of fabric, such as example top fabric panel 807, shown being stitched together with example bottom fabric panel 809. As also discussed above, the cooling pieces 805 may be at least partially enveloped with an insulating material, in some embodiments.

The plurality of interior chambers 803 may be positioned in an array to cover, press against and cool particular regions of the face, such as the eyes, forehead, temple, ears, cheeks and nose, as discussed above. In some embodiments, a plurality of channels, such as the example channels 811 (e.g., voids formed by stitching the plies of fabric, and filled with air), may run between the plurality of chambers, permitting the mask to conform with and exhaust heat and vapor at or about other areas of the face. The plurality of interior chambers may be constructed with a knit fabric, rather than a woven fabric, or an elastic, or relatively elastic fabric or other material, e.g., formed by stitching one or more interior panels of such a fabric, in some embodiments. In such embodiments, the cooling pieces may be tightly packed, stretching the walls of interior chambers 803, due to the stretchability of such a knit or elastic fabric, yet stitching can still be accomplished by manually pushing cooling pieces 805 to one side of such a chamber, and stitching the other side (e.g., to seal of and finish making such a chamber). To aid in such tight packing, in some embodiments, a funnel 813 may be used to guide and push the cooling pieces into each chamber, for example, when the chambers remain open on one side (as pictured for example unfinished chambers 815) prior to completing a final stitch, sealing them (as shown for example filled, completed chambers 817.)

In some embodiments, the sleep masks into which grid 801 is integrated or attached may also include a shaped insulation barrier, protecting the plurality of chambers from external heat transfer in certain areas, while encouraging heat transfer (i.e., cooling the user's face) in other regions.

In some embodiments, cooling pieces 805 may be round or rounded, as pictured, and may be of a size relative to interior chambers at or about the relative size pictured. As an example, each of the cooling pieces pictured are shown to be spherical, or approximately spherical (e.g., in the form of beads). In various embodiments, however, cooling pieces 805 may take on a wide variety of sizes and shapes, which may or may not be rounded, uniform or matching one another. For example, in some embodiments, such cooling pieces may have edges. As another example, in some embodiments, the cooling pieces may have a non-rounded or semi-rounded shape. As another example, in some embodiments, such cooling pieces may have curved edges. As another example, in some embodiments, such cooling pieces may be between 1 and 2 millimeters in diameter. In some embodiments, however, such cooling pieces may be of a larger or smaller size than a sphere between 1 and 2 millimeters in diameter. For example, in some embodiments, such cooling pieces may be microbeads, having a diameter larger than 0.1 micrometer and 5 millimeters.

In some embodiments, any of the above-described cooling pieces include material(s) with a relatively high density and cooling capacity. For example, at least some such material(s) may have a relatively high specific heat, such as glass, stone, sand, ceramics, granite, water, aluminum, other metals and alloys (e.g., steel, magnesium), salts, and plastics (e.g., polyethylene). Preferably, such materials also have especially good thermal conductivity, in some embodiments, including such materials (e.g., soapstone, marble, basalt, steel). Even more preferably, such materials have a higher density, to apply weight to a user's face and in particular areas thereof, for reasons that will be discussed in greater detail below. Also preferably, such materials are sustainably produced materials and/or materials having a low or otherwise more beneficial environmental impact than other materials. For example, in some embodiments, such sustainably produced materials comprise or are created from algae. For example, in some embodiments, such sustainably produced materials comprise or are created from seaweed. As another example, in some embodiments, such sustainably produced materials comprise or are created from agar. As another example, in some embodiments, such sustainably produced materials comprise or are created from carrageenan. As another example, in some embodiments, such sustainably produced materials comprise or are created from any suitable, known hydrocolloid. As another example, in some embodiments, such sustainably produced materials comprise or are created from any suitable, known polymer. As another example, in some embodiments, such sustainably produced materials comprise or are created from any suitable, known compostable plastic. As another example, in some embodiments, such sustainably produced materials comprise or are created from any suitable, known biodegradable plastic. As another example, in some embodiments, such sustainably produced materials comprise or are created from any suitable, known bioplastic.

In some embodiments, such materials include a porous material and/or structure (e.g., lava stones, clays and sands), and may be filled or otherwise treated with a health-enhancing substance, such as essential oil, vitamin E, aloe vera, and moisturizers. In some embodiments, such porous materials may be filled or otherwise treated with a pleasant-smelling substance, such as a fragrance, essential oil, terpenes, and/or fragrance oil. In some embodiments, other materials, such as a fill material or porous panel or insert (e.g., made from a textile) may be otherwise included within the sleep mask, and may be sprayed or otherwise treated with such a health-enhancing and/or pleasant-smelling substance. In some embodiments, such a panel or insert may be removed and replaced from a specialized diffusion chamber, within the sleep mask.

Figure 9:
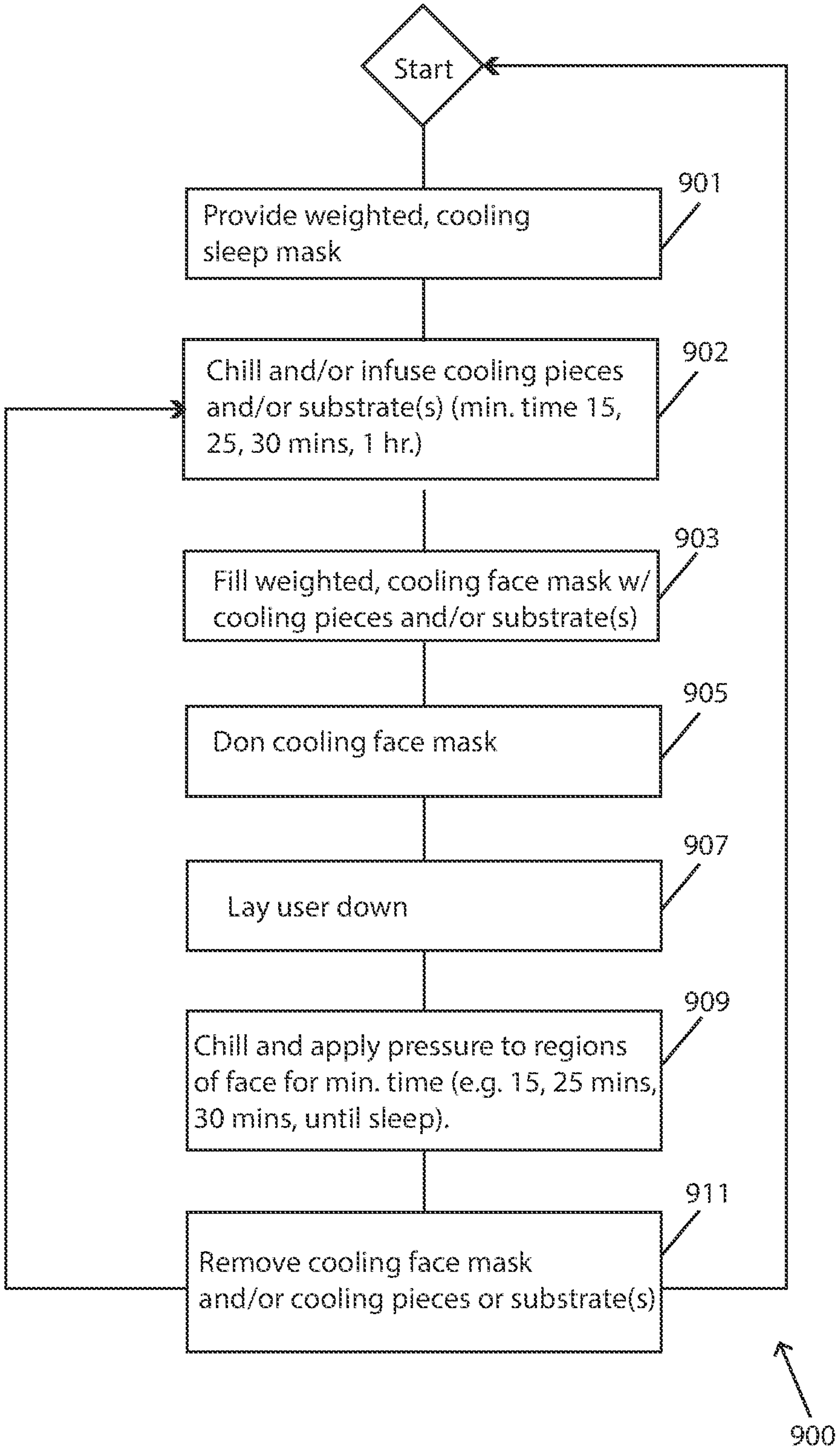
FIG. 9 is an exemplary process flow diagram, including example steps that may be taken to use a cooling- and pressure-applying sleep mask, in accordance with aspects of the present invention.

FIG. 9 is an example process flow diagram of example steps 900 that may be taken by an administrator (e.g., a health care professional) of a weighted, cooling sleep mask, such as any of the weighted, cooling sleep masks set forth in the present application.

In some embodiments, at step 901, the process begins when an administrator of a weighted, cooling sleep mask, such as any of the weighted, cooling sleep masks set forth in the present application, provides such a weighted, cooling sleep mask, for use by a user. In some embodiments, such a user is a human user, using the sleep mask for cooling and applying pressure (e.g., weight and/or tension applied, at least in part, by cooling pieces filling interior chambers of the sleep mask, as discussed above). In some embodiments, the user is a person. In some embodiments, the administrator and the user may be the same person.

Proceeding to step 902, in some embodiments, the administrator and/or user next may chill (lower the temperature of) the cooling pieces. For example, in some embodiments, the administrator and/or user places the cooling pieces, and/or a removable, interior panel including the cooling pieces, from a refrigerator or other cold storage area.

Proceeding to step 903, in some embodiments, which will be discussed in greater detail below, the administrator and/or a user may load the sleep mask with cooling pieces, or may load interior chambers filled with cooling pieces and/or an insertable/removable panel including cooling pieces into the sleep mask.

Proceeding to step 905, in some embodiments, the administrator and/or user next may prepare for rest, stress-relief and/or rejuvenation using the sleep mask, by donning the sleep mask (for example, placing the sleep mask on and about her or his head and face, as shown in FIG. 7). In so donning the sleep mask, the administrator and/or user may also position the interior chambers on or about corresponding regions of her or his face and head, as discussed above.

Proceeding to step 907, in some embodiments, the user may then lay down or recline, for example, on a bed or chair. Preferably, the user lays down or reclines on her or his back, but may also lay on her or his side, or in a prone position, in some embodiments.

Proceeding to step 909, in some embodiments, the administrator and/or user may leave the sleep mask so positioned on her or his face and head for a minimum amount of time, to allow for adequately cooling the user's face and head. For example, in some embodiments, the administrator and/or user leaves the sleep mask so positioned on the user's face and head for at least 15 minutes. As another example, in some embodiments, the administrator and/or user leaves the sleep mask so positioned on the user's face and head for at least 25 minutes. As another example, in some embodiments, the administrator and/or user leaves the sleep mask so positioned on the user's face and head for at least 30 minutes. As another example, in some embodiments, the administrator and/or user leaves the sleep mask so positioned on the user's face and head for at least 45 minutes. As another example, in some embodiments, the administrator and/or user leaves the sleep mask so positioned on the user's face and head for at least 1 hour. As another example, in some embodiments, the administrator and/or user leaves the sleep mask so positioned on the user's face for the duration of a time spent sleeping or resting, however long that may be (e.g., a nap or overnight rest or sleep).

At the end of the duration of application, as set forth in step 909, above, the administrator and/or user may then remove the sleep mask and/or, in some embodiments, removable panel(s) including interior chambers and/or cooling pieces as set forth in the present application, and again chill the sleep mask and/or removable panels, and/or cooling pieces, returning to step 902.

In some embodiments, the process may restart, either with the same, or an additional sleep mask.

Although examples related to using weighted, cooling sleep masks set forth in the present application as a cooling device are provided, it should be understood that, in some embodiments, such weighted, cooling sleep masks may also be used for applying warmth and heat to a user's face and head, and to particular regions thereof discussed above. In such embodiments, any of the steps set forth above related to chilling cooling pieces, such as step 902, set forth above, may be performed by heating, rather than cooling, the cooling pieces to a temperature above—and, in some embodiments, significantly above—room temperature. In some such embodiments, the heated sleep mask may then be applied to a user's face and head for a minimum amount of time, to allow for adequately warming the user's face and head.

The embodiments discussed with reference to the figures are illustrative only, and do not exhaust the many possibilities that fall within the scope of the invention. In some embodiments, for example, any of the steps may be omitted, rearranged, made conditional on other steps, or changed in number or order. Any such alternatives are within the scope of the invention, as will be apparent to those of ordinary skill in the art.

Figure 10:
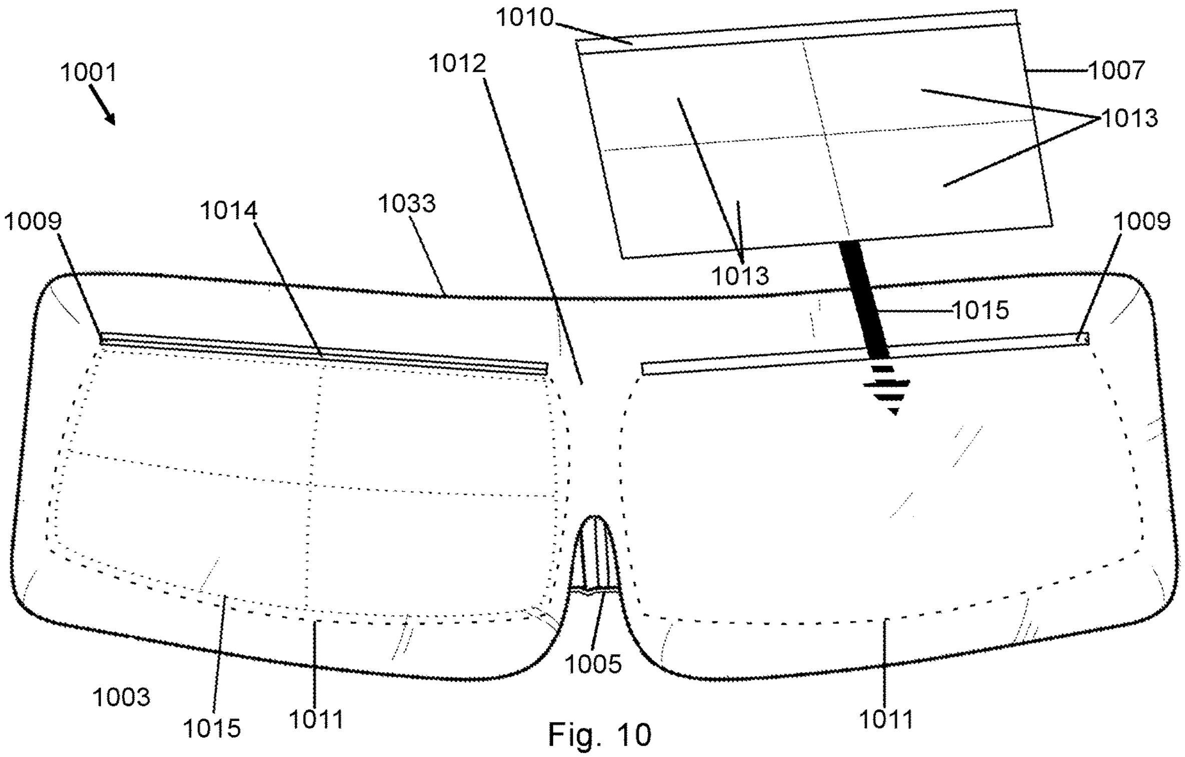
FIG. 10 is a front view of an example weighted, cooling sleep mask, similar to those discussed in reference to FIGS. 1-9, above, but including additional aspects of the present invention related to insertable, removeable substrates for diffusing fragrances and oils.

FIG. 10 is a front view of an example weighted, cooling sleep mask 1001, similar to those discussed in reference to FIGS. 1-9, above, but including additional aspects of the present invention related to insertable, removeable substrates for diffusing fragrances and oils. As with other example weighted, cooling sleep masks set forth in the present application, weighted, cooling sleep mask 1001 may include any or all of component(s), material(s) and structure(s) set forth above, with reference to cooling sleep mask 101, cooling sleep mask 201, cooling sleep mask 301, cooling sleep mask 401, cooling sleep mask 501, cooling sleep mask 601 and cooling sleep mask 701, and with reference to weighted, cooling sleep masks set forth elsewhere in this application. Thus, and again visible in the present figure, is a head-wrapping eye-shield, now shown as example eye shield 1003, which comprises wrapping ends (not fully visible in the front perspective of FIG. 10), and an example elastic headband 1005.

In addition, in some embodiments, one or more insertable, removable substrate(s) 1007 may be provided. In some such embodiments, insertable, removable substrate(s) 1007 may be inserted and/or removed, e.g., via opening(s) 1009, from a user-accessible, substrate-receiving pocket(s) 1011, which, in some embodiments, comprises a cavity fitting insertable, removable substrate(s) 1007 within it, and within weighted, cooling sleep mask 1001. In some embodiments, a structurally reinforced area 1010 is provided, serving as an accessible tab 1014 that remains accessible to a user's fingers (extending into or even slightly out of one of openings 1009 through which it was inserted) even when removable substrate(s) 1007 are inserted to the maximum amount possible into pocket(s) 1011 through openings 1009, as pictured for inserted substrate 1016. In some embodiments, a plurality of such user-accessible, substrate-receiving pocket(s) 1011 are provided, such as the example user-accessible, substrate-receiving pocket(s) shown as 1011. However, in some embodiments, as shown, for example, in FIG. 12, below, a single user-accessible, substrate-receiving pocket may be provided in a weighted, cooling sleep mask such as any of the weighted, cooling sleep masks set forth in this application. In additional, alternative embodiments, however more than two such pockets (e.g., 3, 4, 5, 6, or 7 pockets, in various embodiments) may be so provided. Regardless of the number of such pocket(s) provided in a particular embodiment, any or all of such pocket(s) may have opening(s) similar in nature to openings 1009, which are user-accessible, being disposed on an exterior surface (e.g., an inward- or outward-facing exterior surface, in certain embodiments) of the weighted, cooling sleep mask. In some embodiments, even if such opening(s) 1009 are provided on an outward-facing exterior surface, such as example outward-facing exterior surface 1012, of weighted, cooling sleep mask 1001, user-accessible, substrate-receiving pocket(s) 1011 may abut an inward-facing exterior surface of weighted, cooling sleep mask 1001, or may abut the user's face, when donned. In some embodiments, even if user-accessible, substrate-receiving pocket(s) 1011 do not abut an inward-facing exterior surface of weighted, cooling sleep mask 1001, nor abut the user's face, when donned, user-accessible, substrate-receiving pocket(s) 1011 and/or insertable, removable substrate(s) 1007 may be provided on a side of weighted, cooling sleep mask 1001 facing a user, when donned.

In some embodiments, user-accessible, substrate-receiving pocket(s) 1011 are provided in a shape and size fitting, and complementary to, insertable, removable substrate(s) 1007, which therefore may be put into, and/or removed from, user-accessible, substrate-receiving pocket(s) 1011. Because insertable, removable substrate(s) 1007 can be put into, and/or removed from, user-accessible, substrate-receiving pocket(s) 1011, in some embodiments, insertable, removable substrate(s) 1007 can be separately washed, in some such embodiments, and infused with a health-enhancing and/or pleasant substance, after being removed from weighted, cooling sleep mask 1001, in some embodiments. In some embodiments, insertable, removable substrate(s) 1007 may include interior chambers, such as the examples shown as interior chambers 1013. In some embodiments, as with other interior chambers set forth in the present application, such chambers may be filled with cooling pieces, such as any of the example cooling pieces or types of cooling pieces discussed in this application. In some such embodiments, such cooling pieces may be porous, and are able to be infused with such health-enhancing and/or pleasant substance(s). In other embodiments, insertable, removable substrate(s) 1007 do not comprise cooling pieces, however. In some embodiments, any of the interior chambers, and/or cooling pieces, if provided, are filled or otherwise treated with a health-enhancing substance, such as essential oil, vitamin E, aloe vera, lotion(s) and moisturizer(s). In some embodiments, any of the interior chambers may be filled or otherwise treated with a pleasant-smelling substance, such as a fragrance, essential oil, terpenes, and/or fragrance oil. However, preferably, in some embodiments, such a pleasant-smelling substance may be provided on or about interior chambers 1013 specifically.

In any event, in some embodiments, insertable, removable substrate(s) 1007 are constructed from one or more plies of material (e.g., a porous fabric that can be infused with such health-enhancing and/or pleasant substance(s)). In some embodiments, such a material is any material known in the art that is suitable for use for essential oil diffusion and/or fragrance oil diffusion, when infused with an essential oil or fragrance oil. In some embodiments, insertable, removable substrate(s) 1007 also includes one or more stiff structural elements (e.g., a sheet(s) or a rod(s)) allowing insertable, removable substrate(s) 1007 to be more easily inserted into user-accessible, substrate-receiving pocket(s) 1011, for example, in the direction shown by example insertion direction arrow 1015.

Figure 11:
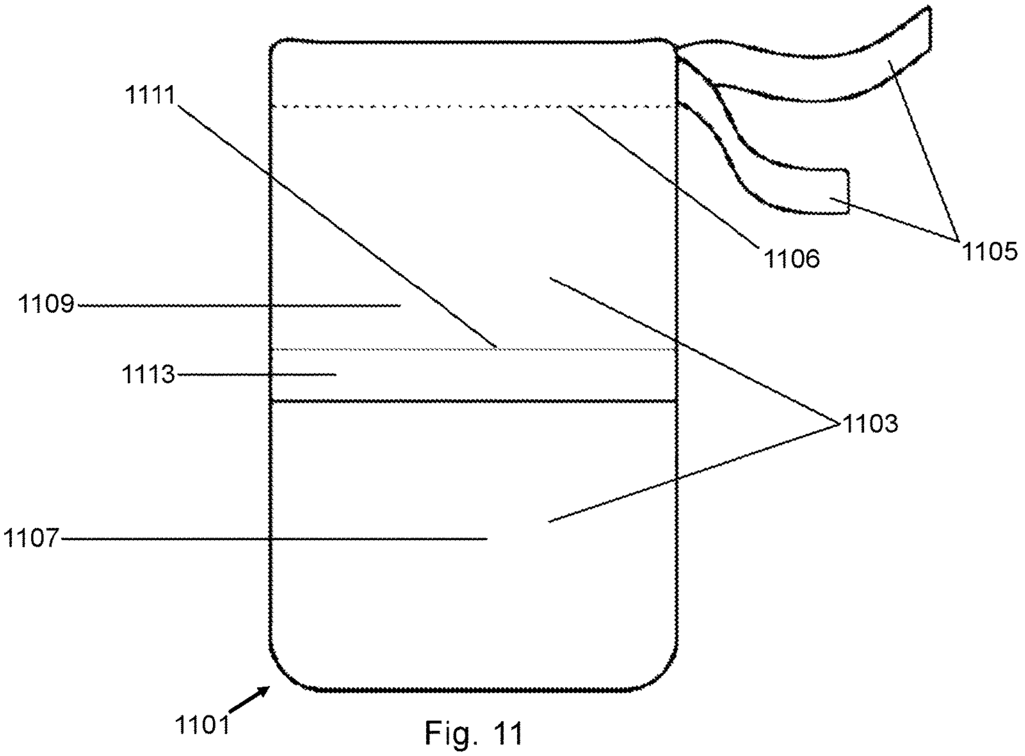
FIG. 11 is a side view of an example carrying bag, including a central compartment and a drawstring, suitable for, among other things, covering and carrying a weighted, cooling sleep mask, in accordance with some embodiments.

FIG. 11 is a side view of an example carrying bag 1101, including a main internal compartment 1103 and a drawstring 1105 (e.g., held within a tunnel 1106), suitable for, among other things, covering and carrying a weighted, cooling sleep mask, such as any of the weighted, cooling sleep masks set forth in the present application, in accordance with some embodiments. As mentioned above, in some embodiments, a carrying bag such as example carrying bag 1101 may be included, with a main internal compartment 1103 of a size suitable for holding and completely covering a weighted, cooling sleep mask, such as weighed, cooling sleep mask 1001, discussed immediately above. In some embodiments, such a carrying bag includes at least one silk exterior panel (e.g., 100% washable silk). In some embodiments, such a carrying bag includes a draw string. In some embodiments, such a carrying bag is approximately 9 to 10 inches (e.g., 9.5 inches) in length. In some embodiments, such a carrying bag is approximately 5.5 to 6.5 inches (e.g., 6 inches) in width. In some embodiments, such a carrying bag includes an auxiliary pocket 1107, opening on an outer surface 1109 of carrying bag 1101. In some such embodiments, such an additional pocket is approximately 3 to 5 inches (e.g., 4 inches) in length. In some embodiments, such a pocket is a reverse-entry pocket, meaning that the pocket's otherwise open end 1111 is covered by a flap of material 1113, e.g., folded over the otherwise open end 1111, creating a new opening directed in an opposite direction (180 degrees from the direction of the otherwise open end).

Figure 12:
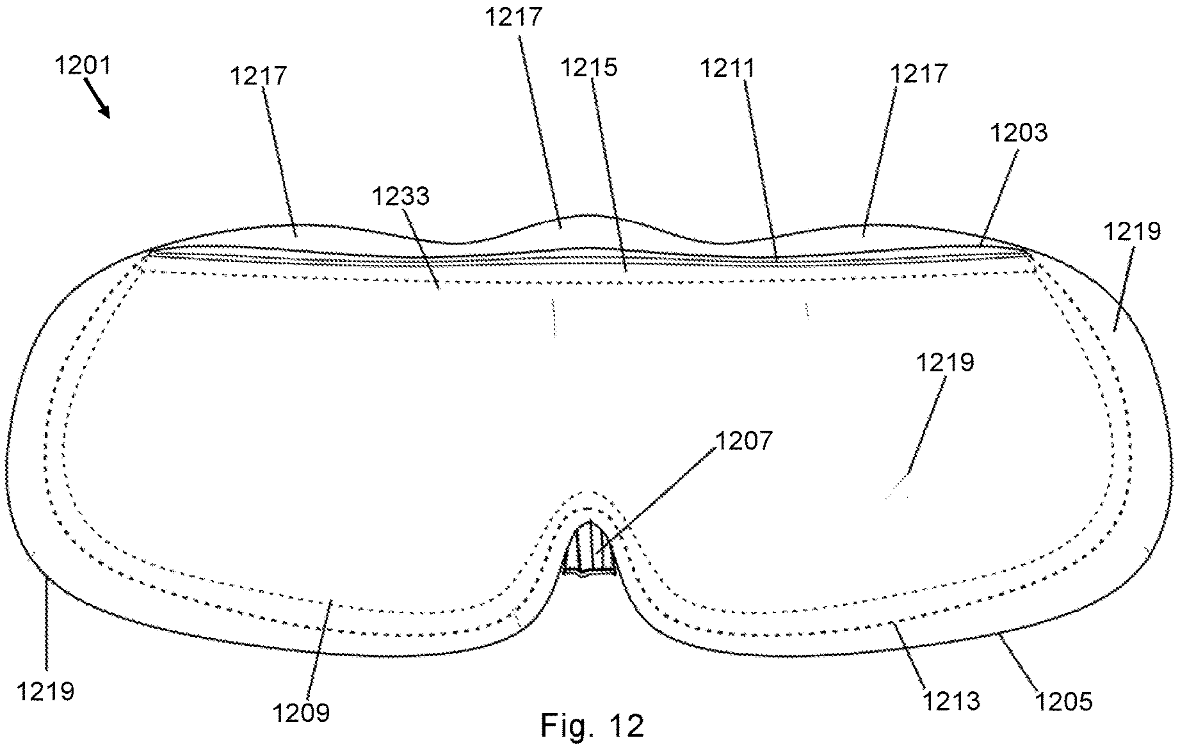
FIG. 12 is a front view of an example weighted, cooling sleep mask 1201, similar to any of those discussed in reference to FIGS. 1-10, above, including additional aspects of the present invention related to insertable, removeable substrates for diffusing fragrances and oils.

FIG. 12 is a front view of an example weighted, cooling sleep mask 1201, similar to any of those discussed in reference to FIGS. 1-10, above, including additional aspects of the present invention related to insertable, removeable substrates for diffusing fragrances and oils. More specifically, example weighted, cooling sleep mask 1201 exhibits a single user-accessible, substrate-receiving pocket 1203, which may be provided in a weighted, cooling sleep mask such as any of the weighted, cooling sleep masks set forth in this application.

As with other example weighted, cooling sleep masks set forth in the present application, weighted, cooling sleep mask 1201 may include any or all of component(s), material(s) and structure(s) set forth above, with reference to cooling sleep mask 101, cooling sleep mask 201, cooling sleep mask 301, cooling sleep mask 401, cooling sleep mask 501, cooling sleep mask 601, cooling sleep mask 701 and cooling sleep mask 1001, and with reference to weighted, cooling sleep masks set forth elsewhere in this application. Thus, and again visible in the present figure, is a head-wrapping eye-shield, now shown as example eye shield 1205, which comprises wrapping ends (not fully visible in the front perspective of FIG. 12), and an example elastic headband 1207.

In addition, in some embodiments, one or more insertable, removable substrate(s), such as example insertable, removable substrate 1209, may be provided, which may be similar in nature to, and include any of the aspects set forth elsewhere in this application from substrates. In some such embodiments, insertable, removable substrate 1209 may be inserted and/or removed, e.g., via a single opening 1211, from a user-accessible, substrate-receiving pocket 1213, which, in some embodiments, comprises a cavity fitting insertable, removable substrate 1209 within it. As discussed above, in some embodiments of weighted, cooling sleep masks in accordance with aspects of the present application, a plurality of such user-accessible, substrate-receiving pocket(s) are provided, such as the example user-accessible, substrate-receiving pocket(s) shown as 1011, above. However, in FIG. 12, example weighted, cooling sleep mask 1201 exhibits a single user-accessible, substrate-receiving pocket 1203, with a single opening 1215. In some embodiments, a single insertable, removable substrate 1209 is provided, with a size and shape complementary to, and fitting, substrate-receiving pocket 1213. In some embodiments, single insertable, removable substrate 1209 includes a weighted bridge 1215, which may have a higher density and/or apply a greater weight or pressure per area to a user's face, when weighted, cooling sleep mask 1201 is donned, than other parts of insertable, removable substrate 1207. As a result, in some embodiments, weighted bridge 1215 fits into more robust receiving areas of weighted, cooling sleep mask 1201, which more robust receiving areas include structurally reinforced, enlarged swells 1217 of the weighted, cooling sleep mask 1201, in some embodiments. In some embodiments, weighted bridge 1215 and/or enlarged swells 1217 create greater inward pressure, in pounds per square inch, against areas of a user's head and face abutting them, than the remainder of weighted, cooling sleep mask. In some methods in accordance with aspects of the present application, weighted bridge 1215 and/or enlarged swells 1217 create such greater inward pressure activates pressure points of the user's nasal bridge and brow areas, respectively, which may be used to avert or reduce pain and, in particular, pain from migraines and/or tension headaches.

In some embodiments, weighted, cooling sleep masks are provided in a wide range of different overall shapes than that pictured above, while still carrying out aspects of the invention—as will be readily apparent to those of skill in the art. For example, as shown for weighted, cooling sleep mask 1201, more greatly curved outer surfaces 1219 than depicted previously for weighted, cooling sleep masks, may be provided, in some embodiments.

Similarly, in some embodiments, a different number, arrangement, and/or order, or layering of interior chambers, than those examples, discussed above, may be provided—again, as will be readily apparent to those of skill in the art. For example, some such other, alternative embodiments of interior chambers, and air-filled voids (also serving as folding areas, in some embodiments) provided between them, in some embodiments, are provided below, in reference to FIG. 13.

Figure 13:
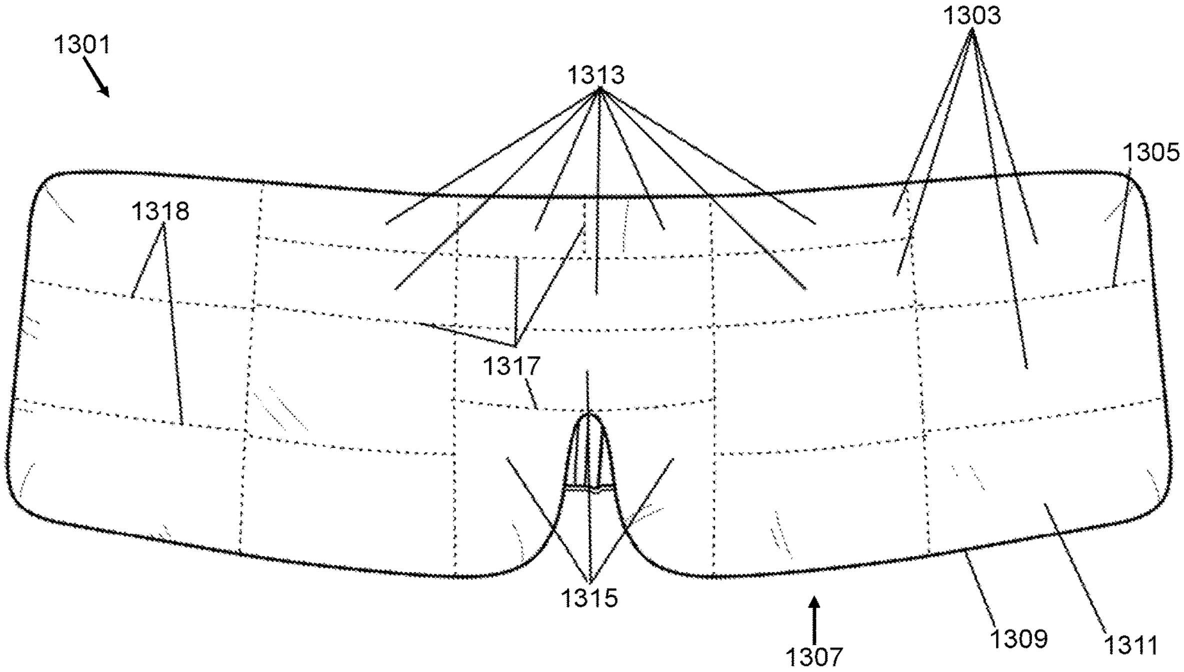
FIG. 13 is a front view of another example weighted, cooling sleep mask, similar in nature to that discussed in reference to FIGS. 1-7 and 10, above, illustrating additional aspects of the present invention.

FIG. 13 is a front view of another example weighted, cooling sleep mask 1301, similar in nature to that discussed in reference to FIGS. 1-7 and 10, above, illustrating additional aspects of the present invention. In at least some embodiments, cooling sleep mask 1301 may include any or all of component(s), material(s) and structure(s) set forth above, with reference to cooling sleep masks 101, 201, 301, 401, 501, 601, 701, 1001 and with reference to weighted, cooling sleep masks set forth elsewhere in this application. In some embodiments, as mentioned above, such a sleep mask includes a plurality of interior chambers, loaded with cooling pieces (such cooling pieces not being pictured in the present figure), such as example interior chambers 1303, which, as with other interior chambers set forth in the present application, may be formed by stitching together two or more interior layers of fabric 1305, held within a main body 1307 of sleep mask 1301. Such a main body 1307 may be include a housing 1309, formed by one or more exterior panel(s) 1311, which may be, or be similar to, exterior panel 107 and exterior panel 109, discussed above, including any of the same, or similar material(s).

As discussed above, in some embodiments, such interior chambers are the same or similar in size and/or shape. However, in some embodiments, as pictured in the present figure, such interior chambers, as shown for interior chambers 1303, instead are provided in different sizes and shapes. For example, in some embodiments, there are a greater number per unit of area, of smaller interior chambers—namely smaller chambers 1313—filling a brow region of weighted, cooling sleep mask 1301. Similarly, in some embodiments, there are a greater number per unit of area, of smaller interior chambers—namely smaller chambers 1315—filling a nasal region of weighted, cooling sleep mask 1301. In some embodiments, each of smaller chambers 1313 and smaller chambers 1315 may hold fewer cooling pieces than others of interior chambers 1303.

However, in some embodiments, smaller chambers 1313 and/or smaller chambers 1315 may hold a higher density of cooling pieces (number of cooling pieces per unit of volume) despite holding a smaller number of cooling pieces than others of interior chambers 1303. For example, in some embodiments, smaller chambers 1313 hold a higher density of cooling pieces (number of cooling pieces per unit of volume) while holding a smaller number of cooling pieces than others of interior chambers 1303. As another example, in some embodiments, smaller chambers 1315 hold a higher density of cooling pieces (number of cooling pieces per unit of volume) while holding a smaller number of cooling pieces than others of interior chambers 1303. As yet another example, other sub-set(s) of interior chambers 1303 hold a higher density of cooling pieces (number of cooling pieces per unit of volume) while holding a smaller number of cooling pieces than others of interior chambers 1303. Also, in some embodiments, smaller chambers 1313 and/or smaller chambers 1315 may hold a different type(s) of cooling pieces than others of interior chambers 1303. For example, in some embodiments, smaller chambers 1313 hold a different type(s) of cooling pieces than others of interior chambers 1303. As another example, in some embodiments, smaller chambers 1315 hold a different type(s) of cooling pieces than others of interior chambers 1303. In some such embodiments, such different type(s) of cooling pieces may be particularly porous cooling pieces, more able to absorb and diffuse scents and other beneficial fluids. For example, in some embodiments, such particularly porous cooling pieces are provided within smaller chambers 1313 (at the brow region). As another example, in some embodiments, such particularly porous cooling pieces are provided within smaller chambers 1315 (at the nasal region). In some embodiments, such different type(s) of cooling pieces may be particularly dense cooling pieces, more able to apply pressure to areas of a user's face. For example, in some embodiments, such particularly dense cooling pieces are provided within smaller chambers 1313 (at the brow region). As another example, in some embodiments, such particularly dense cooling pieces are provided within smaller chambers 1315 (at the nasal region).

In some embodiments, smaller chambers 1313 and/or smaller chambers 1315 are provided between different lines of stitching, such as the example lines of stitching 1317, than others of interior chambers 1303. Similarly, in some embodiments, other interior chambers 1303 are provided between different lines of stitching, such as example lines of stitching 1318, than set forth for other weighted, cooling sleep masks set forth in the present application. In some embodiments, such different lines of stitching 1317 coincide with at least some different, less continuous, smaller, and less-open channels (air-filled voids) on or about them (e.g., in the space about 1/16 to 1/4 inch, surrounding them), than present in other weighted, cooling sleep masks set forth in the present application. In some embodiments, such different lines of stitching 1318 result in the creation of at least some different, less continuous, smaller, and less-open channels (air-filled voids) on or about them (e.g., in the space about 1/16 to 1/4 inch, surrounding them), than present in other weighted, cooling sleep masks set forth in the present application.

Figure 14:
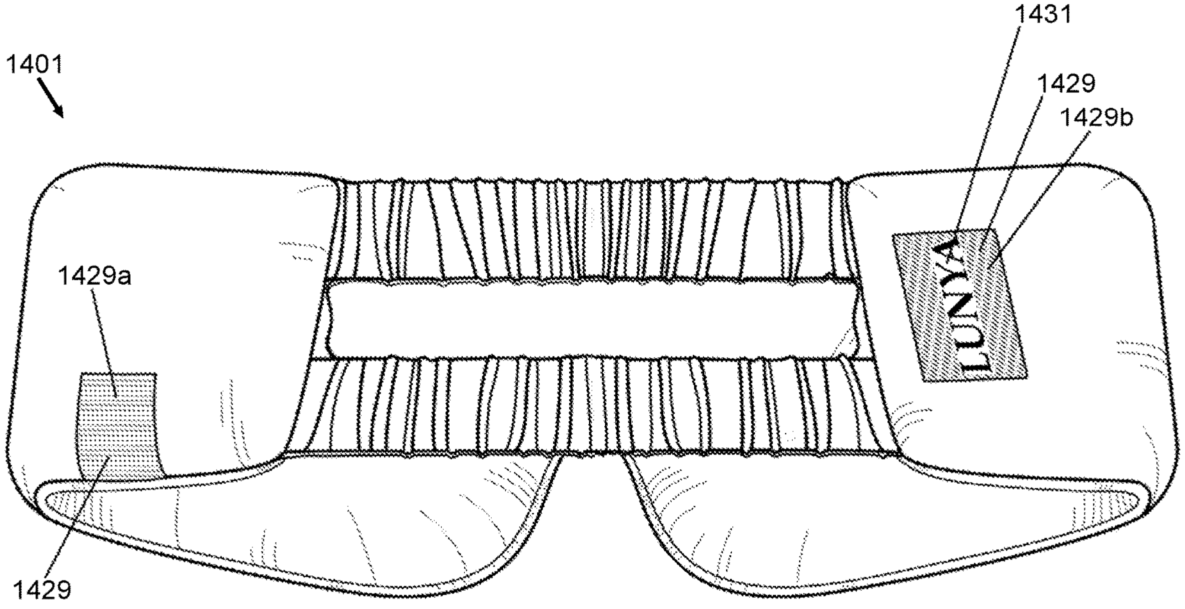
FIG. 14 is a front view of another example weighted, cooling sleep mask, similar in nature to that discussed in reference to FIG. 1, above, illustrating additional aspects of the present invention.

FIG. 14 is a front view of another example weighted, cooling sleep mask 1401, similar in nature to that discussed in reference to FIG. 1, above, illustrating additional aspects of the present invention. In at least some embodiments, weighted, cooling sleep mask 1401 may include any or all of component(s), material(s) and structure(s) set forth above, with reference to weighted, cooling sleep mask 101, and with reference to weighted, cooling sleep masks set forth elsewhere in this application. For example, as with weighted, cooling sleep mask 101, weighted, cooling sleep mask 1401 includes at least partially decorative panels, now shown as decorative panels 1429, which may include any of the materials, and be used in the same way, as other at least partially decorative panels set forth in the present application. However, in some embodiments, at least one of decorative panels 1429 includes different, alternative branding elements than other decorative panels set forth in the present application. For example, decorative panel **1429*b* is pictured as including a new form of decorative panel, with a different, alternative brand element 1431, than that discussed above for other weighted, cooling sleep masks (e.g., different than brand or other identifier 131**, discussed above).

In some embodiments, such an identifier may indicate one of a plurality of sizes, weights, applications, or other appropriate user types for sleep mask 1401 which are different from such user types for at least some other embodiments of weighted, cooling sleep masks set forth in the present application. For example, in some embodiments, decorative panel **1429*b* includes a brand and/or identifier 1431** which may indicate that weighted, cooling sleep mask is appropriate for use by women, rather than men, being of a smaller size and weight, or containing different materials than other weighted, sleep masks set forth in this application, and being more appropriate for use by women.

We claim:

1. A device for aiding in rest, comprising:

a lower portion, comprising a notch, adapted for accommodating and applying pressure to, and surrounding, both a bridge and wings of a user's nose;

an upper portion, located vertically above and forming a single, unitary piece with, the lower portion, which upper portion and which lower portion comprise a first plurality of interior chambers and a second plurality of interior chambers, respectively;

dual elastomeric head bands, each attached to or integral with ends of said upper portion;

wherein the first plurality of interior chambers and the second plurality of interior chambers are each filled with a plurality of cooling pieces, comprising a material with a relatively high specific heat, and comprise a hybrid arrangement of chambers, having different shapes and alignments, said hybrid arrangement of chambers comprising some chambers aligned with each other longitudinally, and other chambers aligned with each other transversely; and wherein said notch is defined by at least part of each of a subset plurality of interior chambers of said second plurality of interior chambers.

2. The device for aiding in rest of claim 1, wherein said cooling pieces comprise a material including glass.

3. The device for aiding in rest of claim 2, wherein said glass is a recycled glass.

4. The device for aiding in rest of claim 1, wherein said cooling pieces comprise a material including water.

5. The device for aiding in rest of claim 1, wherein said cooling pieces comprise a material including a plant-derived polymer.

6. The device for aiding in rest of claim 5, wherein the cooling pieces comprise a material derived from algae.

7. The device for aiding in rest of claim 1, wherein the first plurality of interior chambers and the second plurality of interior chambers are each configured to apply pressure to and/or absorb heat energy from a different, defined region of the user's head and/or face.

8. The device for aiding in rest of claim 1, wherein each of the first plurality of interior chambers and the second plurality of interior chambers is flattened by rigid fibers placed in a greater concentration at bases of each of the first plurality of interior chambers and the second plurality of interior chambers.

9. The device for aiding in rest of claim 1, wherein the first plurality of interior chambers and/or the second plurality of interior chambers are each flattened by an effect of the cooling pieces held within each of the plurality of interior chambers having different densities.

10. The device for aiding in rest of claim 1, wherein each of the first plurality of interior chambers and/or the second plurality of interior chambers comprises cross-members, bridging between a plurality of walls forming said each of the first plurality of interior chambers and/or the second plurality of interior chambers.

11. The device for aiding in rest of claim 1, wherein at least one of the first plurality of interior chambers and/or the second plurality of interior chambers comprises at least part of a fabric panel and stitching.

12. The device for aiding in rest of claim 11, wherein at least one of the at least one fabric panels comprises a knit fabric.

13. The device for aiding in rest of claim 12, wherein the upper portion and/or the lower portion comprise(s) at least one exterior panel, comprising a flexible, but non-stretch material.

14. The device for aiding in rest of claim 13, wherein the flexible, but non-stretch material comprises silk.

15. A method for enhancing rest, comprising the following steps:

providing a device for aiding in rest, comprising:

a lower portion, comprising a notch, adapted for accommodating and applying pressure to, and surrounding, both a bridge and wings of a user's nose;

an upper portion, located vertically above and forming a single, unitary piece with the lower portion, which upper portion and which lower portion comprise a first plurality of interior chambers and a second plurality of interior chambers, respectively;

dual elastomeric head bands, each attached to or integral with ends of said upper portion;

wherein the first plurality of interior chambers and the second plurality of interior chambers are each filled with a plurality of cooling pieces, comprising a material with a relatively high specific heat, and comprise a hybrid arrangement of chambers, having different shapes and alignments, said hybrid arrangement of chambers comprising some chambers aligned with each other longitudinally, and other chambers aligned with each other transversely; and wherein said notch is defined by at least part of each of a subset plurality of interior chambers of said second plurality of interior chambers.

16. The method for enhancing rest of claim 15, comprising the following additional step(s):

chilling said cooling pieces, to below water-freezing temperatures, in a freezer.

17. The method for enhancing rest of claim 16, comprising the following additional step(s):

donning the device for aiding in rest, and positioning each of the first plurality of interior chambers and each of the second plurality of interior chambers on or about a different, defined region of the user's head and face, applying pressure and absorbing heat energy to the user's head and face.

18. A device for aiding in rest, comprising:

a lower portion, comprising at least two exterior panels of flexible material, and at least two interior plies of flexible material, permanently fastened to and integral with said lower portion, wherein the at least two interior plies of flexible material form a plurality of interior chambers and air-filled voids;

an upper portion, abutting and attached to, or integral with, the lower portion;

at least one elastomeric head band, attached to or integral with ends of said upper portion;

a notch, comprising a linear portion, adapted for accommodating and applying pressure to, and surrounding, both a bridge and wings of a user's nose;

wherein each of the plurality of interior chambers are each filled with a plurality of cooling pieces comprising a material with a relatively high specific heat, and comprise a hybrid arrangement of chambers, having different shapes and alignments, said hybrid arrangement of chambers comprising some chambers aligned with each other longitudinally, and other chambers aligned with each other transversely.

19. The device for aiding in rest of claim 18, wherein the air-filled voids are at locations causing folding between pressure points of a user's face, and wherein at least one of the at least two exterior panels of flexible material comprises silk.

20. The device for aiding in rest of claim 18, wherein at least some of the cooling pieces comprise materials with a lower density than others of the cooling pieces, causing a more even distribution of cooling pieces at a top and at a base of at least one of the plurality of interior chambers than if all of the cooling pieces had the same density.

* * * * *